(12) United States Patent
Cibelli et al.

(10) Patent No.: US 7,858,308 B2
(45) Date of Patent: Dec. 28, 2010

(54) IDENTIFICATION OF GENES OR POLYPEPTIDES THE EXPRESSION OF WHICH CORRELATES TO FERTILITY, OVARIAN FUNCTION AND/OR FETAL/NEWBORN VIABILITY

(75) Inventors: Jose Cibelli, East Lansing, MI (US); Javier Crosby, Santiago (CL); Emilio Fernandez, Santiago (CL); Arif Kocabas, East Lansing, MI (US); Guilherme Jordao De Magalhaes Rosa, Middleton, WI (US)

(73) Assignee: Michigan State University, East Lansing, MI (US)

( * ) Notice: Subject to any disclaimer, the term of this patent is extended or adjusted under 35 U.S.C. 154(b) by 0 days.

(21) Appl. No.: 11/584,580

(22) Filed: Oct. 23, 2006

(65) Prior Publication Data
US 2007/0238111 A1 Oct. 11, 2007

Related U.S. Application Data

(63) Continuation-in-part of application No. 11/437,797, filed on May 22, 2006, and a continuation-in-part of application No. 11/091,883, filed on Mar. 29, 2005.

(60) Provisional application No. 60/556,875, filed on Mar. 29, 2004.

(51) Int. Cl.
*C12Q 1/68* (2006.01)
*C12P 19/34* (2006.01)
*A01N 43/04* (2006.01)

(52) U.S. Cl. ............ 435/6; 435/91.2; 514/44 R
(58) Field of Classification Search ............ 435/6, 435/91.2; 514/44 R
See application file for complete search history.

(56) References Cited

U.S. PATENT DOCUMENTS

| 7,041,648 B2 | 5/2006 | Mantovani |
| 2003/0124551 A1* | 7/2003 | Pappa et al. ............ 435/6 |
| 2004/0081958 A1* | 4/2004 | Eilertsen et al. ............ 435/6 |
| 2006/0024693 A1 | 2/2006 | Cibelli |
| 2007/0054289 A1 | 3/2007 | Cibelli |

OTHER PUBLICATIONS

Bisseling et al. Fertility and Sterility 68:907-911; 1997.*
NCBI Accession No. AY324387 (Sequence PRI Jun. 24, 2003); pp. 1-6.*
Jansen et al. (eMJA 178: 258-261; 2003.*
International Search Report, PCT Application No. PCT/US07/12157, mailed Sep. 11, 2008, 14 pages.
Jansen, P.S. eMJA 2003 vol. 178, No. 6, pp. 258-261; Abstract.
Mckenzie et al. Human Reproduction vol. 19. No. 12, pp. 2869-2874; Oct. 2004; especially Abstract.
Salustri et al. Development vol. 131. pp. 1577-1586 ; especially 1579 and p. 1586, Mar. 2004.
International Search Report, PCT Application No. PCT/US05/10360, mailed Sep. 29, 2006, 10 pages.
P. Lonergan, et al., "Oocyte and Embryo Quality: Effect of Origin, Culture Conditions and Gene Expression Patterns", Reprod. Dom. Anim., vol. 38, p 259-267, 2003.
Fair et al. Mol. Repr. Dev. 67:136-144; 2004.
Velde et al, The variability of female reproductive ageing; Human Reproduction Update, vol. 8, No. 2, pp. 141-154, (2002).

* cited by examiner

*Primary Examiner*—Fereydoun G Sajjadi
(74) *Attorney, Agent, or Firm*—Hunton & Williams LLP

(57) ABSTRACT

A genetic means of determining whether a female subject produces "pregnancy competent" oocytes is provided. The means comprises detecting the level of expression of one or more genes that are expressed at characteristic levels (upregulated or downregulated) in cumulus cells derived from pregnancy competent oocytes. This characteristic gene expression level, or pattern referred to herein as the "pregnancy signature", also can be used to identify subjects with underlying conditions that impair or prevent the development of a viable pregnancy, e.g., pre-menopausal condition, other hormonal dysfunction, ovarian dysfunction, ovarian cyst, cancer or other cell proliferation disorder, autoimmune disease and the like. Microarrays containing "pregnancy signature" genes or corresponding polypeptides provide another preferred aspect of the invention. Still further, the subject invention can be used to derive animal models, e.g., non-human primate animal models, for the evaluation of the efficacy of putative female fertility treatments.

14 Claims, 31 Drawing Sheets

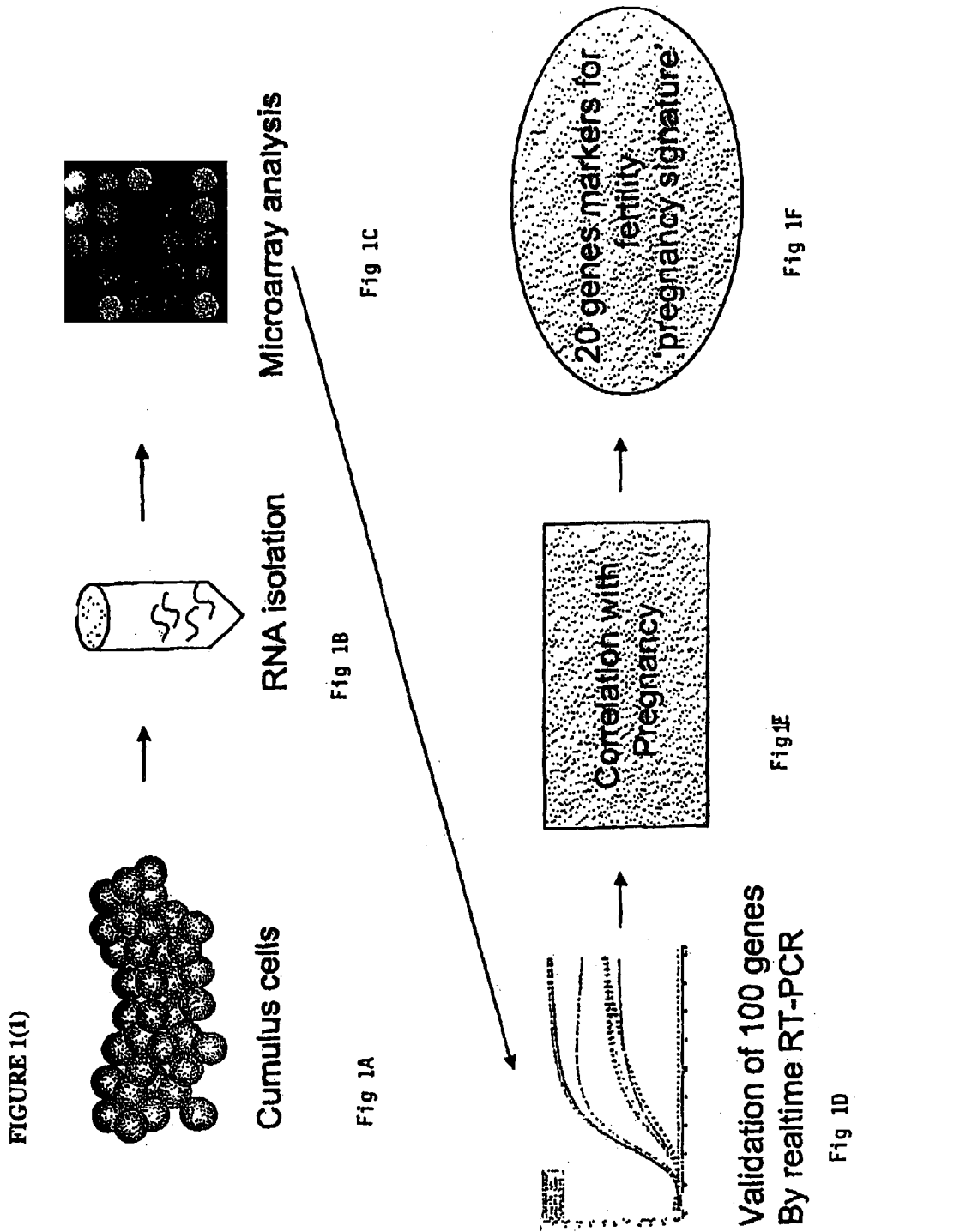

FIGURE 1(2)
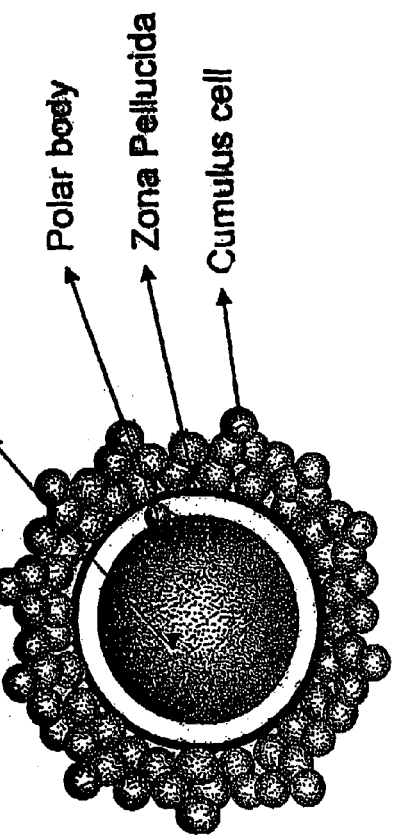
Fig 1G
Freshly ovulated human egg
Polar body
Zona Pellucida
Cumulus cell
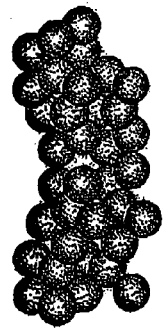
Cumulus cells to be sent
To our laboratory for RNA
profiling
Fig 1I
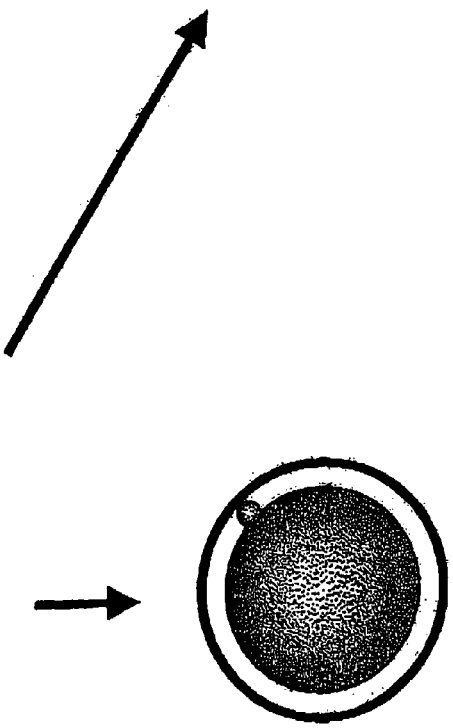
Egg to be fertilized and
Transferred into the uterus
Fig 1H Figure 2.
a
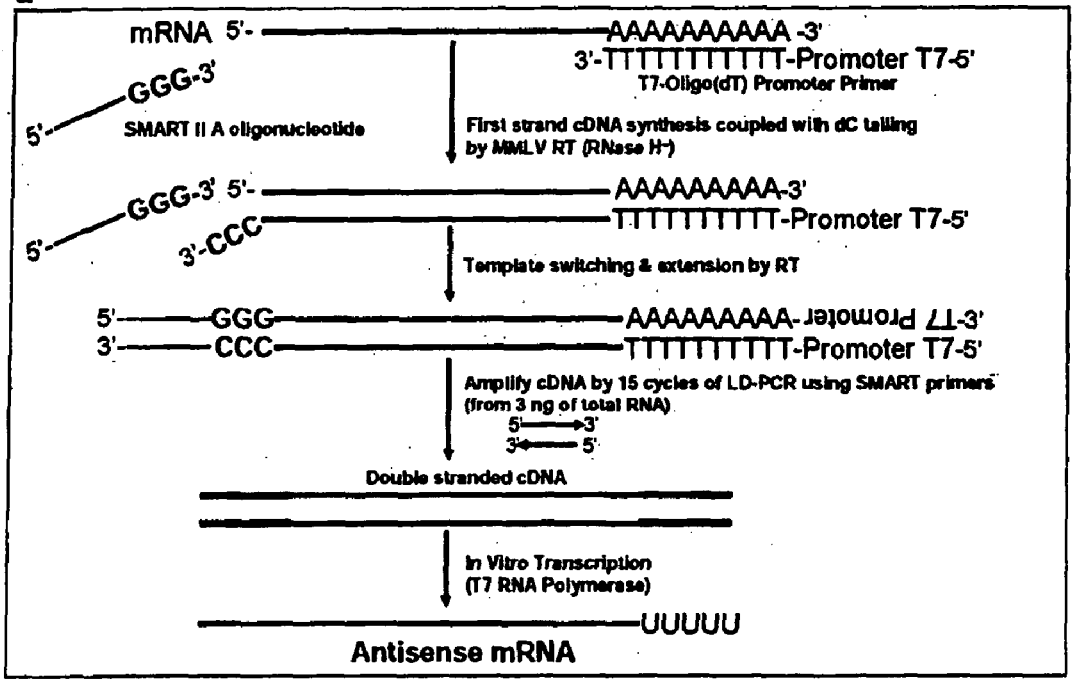
b.
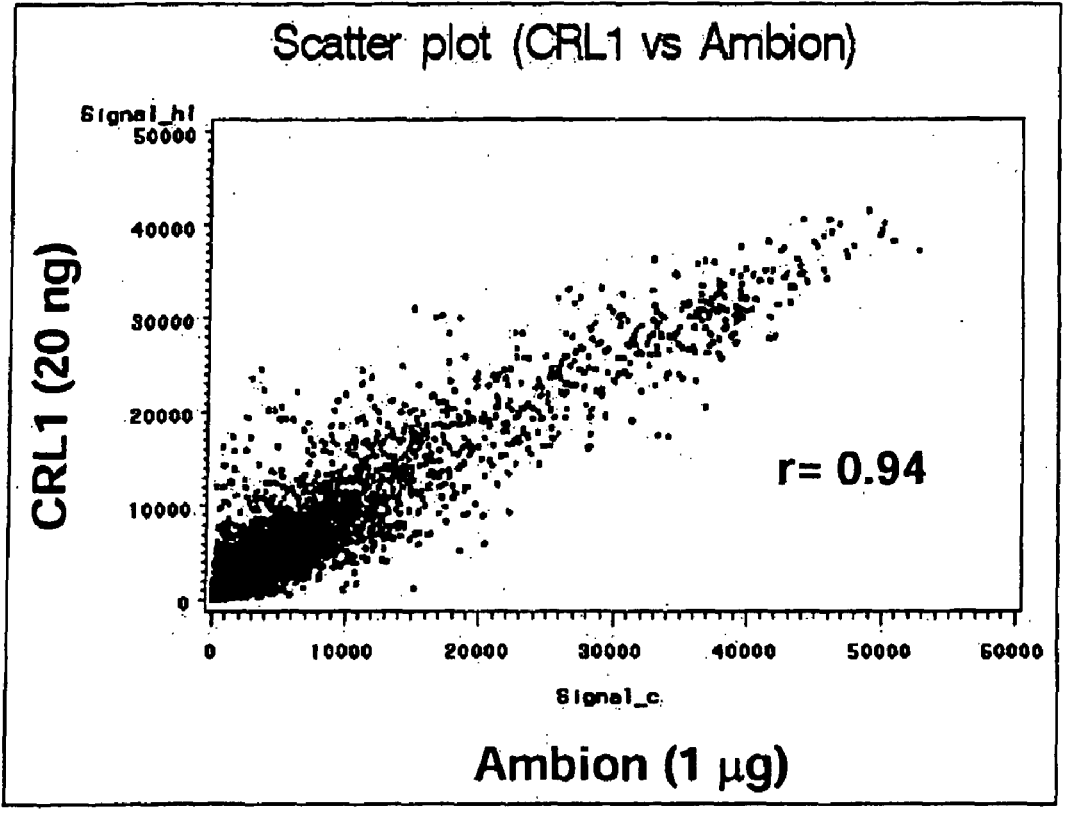

FIGURE 5

| | GO Biological Process term | Representative genes expressed by the human oocyte |
|---|---|---|
| 1 | Cell Cycle<br>  Mitotic cell cycle<br>    M phase<br>    Nuclear division<br>    Cytokinesis<br>  Meiosis<br>    Meiosis I<br>    Meiotic prophase I<br>    DNA recombination<br>    Sister chromatid cohesion<br>  Regulation of cell cycle<br>    Cell cycle checkpoint<br>    Regulation of mitosis | ANAPC1, ANLN, APC10, BIN3, BRCA2, BUB1, BUB1B, BUB3, C2orf6, CCNA2, CCNB1, CCNB2, CCNB3, CCND2, CCNE1, CCNE2, CCNG2, CCNI, CDC14A, CDC20, CDC23, CDC25B, CDC25C, CDC27, CDC45L, CDC5L, CDC7, CDK3, CDK7, CDK8, CENPE, CENPF, CENPH, CETN3, CHC1, CHEK1, CHFR, CKS2, NAP1, CSPG6, EML4, ESPL1, GAJ, GPR125, HCAP-G, HCAP-G, HSPC135, HT014, IDN3, KATNA1, KIF11, KIF23, KIF2C, KNSL7, KNTC1, LIG1, LIG4, MAD2L1, MAD2L2, MAD2L2, MPHOSPH1, MRE11A, MSH5, MVP, NEDD5, NEK1, NEK2, PAFAH1B1, PARD3, PCCB, PLK1, PPP1R9B, PRC1, PREI3, PTTG1, RAD1, RAD17, RAD51L1, RAD54B, RAN, RBM11, SAP30, SKB1, SMC2L1, SMC4L1, STAG3, STK6, SUGT1, SYCP2, TARDBP, TPX2, TTK, UBE2C, UBE2D3, UNG2, ZW10 |
| 2 | Nucleic acid metabolism<br>  DNA metabolism<br>    DNA replication DNA<br>    replication and chromosome<br>    cycle<br>    DNA repair<br>  RNA metabolism<br>    mRNA metabolism<br>    mRNA processing<br>    mRNA catabolism<br>    tRNA metabolism | ACF, CDC45L, CENPE, CENPF, CENPH, CHAF1A, CHAF1B, CPEB1, CPEB4, CPSF2, DNA2L, ESPL1, FEN1, FNBP3, HCAP-G, HNRPA1, IDN3, LIG1, LIG4, MAD2L1, MSH2, MSH3, MSH5, NAP1L1, ORC1L, ORC4L, ORC5L, PABPN1, PCF11, PCNA, PLRG1, POLA, POLB, POLD3, POLE2, POLG2, POLQ, POLS, PRIM2A, PRPF3, PRPF4, PSEN2, RAD17, RBM17, RFC4, SF3B4, SFRS12, SIP1, SLBP, SMN1, SNRPD1, SNRPE, SNRPF, TFAM, TOP1, TOP2A, U2AF2, XRN2 |

FIGURE 5 (Con't)

| 5 | Ubiquitin-dependent protein catabolism<br>Protein modification<br>Ubiquitin cycle | ARIH1, ARIH2, BTRC, CDC20, CDC34, CYLD, DD5, DKFZP564G092, FBXO11, FBXO8, FLN29, FTS, HACE1, HIP2, HSPC150, HSXIAPAF1, LMO7, PSMA2, PSMA5, PSMA7, PSMD9, RNF14, SAE1, SIAH1, SMURF1, STAU2, TSG101, UBE2C, UBE2D3, UBE2G1, UBE2I, UBE2L3, UBE2N, UBE2Q, UBE2R2, UBE2S, UBE3B, UBPH, UCHL1, USP1, USP10, USP13, USP15, USP16, USP2, USP21, USP26, USP30, USP34, USP35, USP36, USP37, USP44, USP49, USP52, USP9X, WWP2 |
|---|---|---|
| 6 | Phosphate metabolism<br>Protein amino acid phosphorylation<br>Protein amino acid dephosphorylation | ACVR1, ACVR1B, ACYP1, AKT2, AURKB, AURKC, BMP2K, BMPR1A, BRAP, BUB1, CAMK1D, CAMK2G, CCRK, CDC14A, CDC25B, CDC25C, CDC42BPA, CDC42BPB, CDC7, CDK3, CDK7, CDK8, CDKL5, CHEK1, CHEK2, CLK1, CLK2, , CLK3, CRK7, CSF1R, CSNK1E, DAPK1, DUSP10, DUSP5, EPHA1, EPHB1, ERN1, FER, FGFR1, FGFR2, FYN, GPR125, GRK6, GSK3A, HMGA1L4, IGF1R, IKBKB, ILKAP, IMPA1, INHBA, INPP5D, KIT, MADH2, MADH5, MAP2K1, MAP4K3, MAPK6, MAPK7, MAPK8, MAPKAPK5, MARK2, MARK4, MASTL, MELK, MKNK1, MOS, MTM1, MTMR3, NEK1, NTRK2, PACE-1, PASK, PDPK1, PLK1, PLK3, PPM1E, PRKAR1A, PRKCG, PRKG1, PRKRA, PTEN, PTK2, PTK9, PTP4A3, PTPN2, PTPN3, PTPRG, PTPRH, PTPRN2, RIOK1, STK24, STK31, STK38, STK6, TEC, TEX14 |
| 7 | Reproduction<br>Sexual reproduction<br>Gametogenesis<br>Spermatogenesis | AXIN1, BCL2L10, BMP15, BRD2, CCNI, CHEK1, CUGBP1, D8S2298E, DAZ, DAZ2, DAZL, DNAH9, FLJ10511, FUT10, GDF9, GMCL, HIST1H1E, HMGCR, HSF2BP,HSPC039 , KHDRBS3, MAGOH, NASP, NDRG3, NJMU-R1, NOC4, NR6A1, NY-REN-24, ODC-p, PIWIL1, PPP1R12A, PTTG1, RNF125, RNF138, SOX30, SPAG6, SPATA2, SPIN, STRBP, TDRD1,TEX15 , TSGA10, TUBD1, USP9X, WFDC2, XRN2, ZP2 |
| 8 | Chromatin remodeling<br>Chromatin modification<br>Non-covalent chromatin modification | ARID1A, ASF1A, ASF1B, BAF53A, BRCA2, CHD4, EHMT1, GCN5L2, HDAC9, HELSNF1, HMG20B, MLL3, MLL4, MSL3L1, SETDB1, SIRT7,SMARCA1 , SMARCA5, SMARCAD1, SMARCC2, SMARCD1 |

FIGURE 7

| Gene | Accession Number | Sequence | Product Size (bp) |
|---|---|---|---|
| OCT4 | NM_002701 | 5'-GAGTGAGAGGCAACCTGGAG-3'<br>5'-GTGAAGTGAGGGCTCCCATA-3' | 274 |
| STELLA | AY317075 | 5'-CTCAAATCTCCTCCGAGACG-3'<br>5'-TGAAGTGGCTTGGTGTCTTG-3' | 385 |
| ESG1 | NM_001025290 | 5'-AGAGGTGTTCCAGGTCCAGA-3'<br>5'-GCTCTGGCCACACCTAATC-3' | 341 |
| VASA | AY004154 | 5'-TGGGACATTCAATTCGACAA-3'<br>5'-GAGAACTGGCCAACTTGGAG-3' | 364 |
| GDF9 | NM_005260 | 5'-CTGCCTATCCTGTGGGAGAA-3'<br>5'-ACTGGAGAGCCATACCGATG-3' | 301 |
| ZP1 | NM_207341 | 5'-GGCTTCTGCAGAGGACAGAC-3'<br>5'-TCGTCGCTGTCTTGTAGTGC-3' | 344 |
| H1FOO | NM_153833 | 5'-AGTCGGGAGAGGCTAGGAAG-3'<br>5'-GTACCACCTTGGACCCACTG-3' | 306 |
| CDH3 | NM_001793 | 5'-GCTACCGCATCCTGAGAGAC-3'<br>5'-TCACCTTCCTCGTTGACCTC-3' | 376 |
| TUB4Q | U83110 | 5'-CTGGTGTCTGCTACCGTGAG-3'<br>5'-GGGAGCCAGTCAGCAAAGTA-3' | 356 |
| ACTB | NM_001101 | 5'-GGCATCCTCACCCTGAAGTA-3'<br>5'-CCATCTCTTGCTCGAAGTCC-3' | 496 |

FIGURE 8

| Gene title | Gene symbol | Reported function(s) in murine oocytes | Reference |
|---|---|---|---|
| developmental pluripotency associated 3 | DPPA3 | Maternal effect gene required for oocyte development | Curr Biol, 2003, 13:2110-7 |
| zona pellucida glycoprotein 1 (sperm receptor); zona pellucida glycoprotein 3 (sperm receptor) | ZP1, ZP3 | Required for successful fertilization in which the sperm must bind and penetrate the ZP; prevention of further sperm entry following fertilization; and prevents blastocyst adherence to oviduct wall as it travels down the uterus | Front Biosci., 2005, 10:2335-45 |
| v-mos Moloney murine sarcoma viral oncogene homolog | MOS | Activation of MAPK cascade that enables progression through oocyte maturation, and subsequent maintenance of meiotic metaphase II arrest | Biochem Biophys Res Commun., 2002, 296:1372-7 |
| growth differentiation factor 9 | GDF9 | Essential for ovarian follicular growth and function | Cell Tissue Res., 2005, 322:107-15; Reproduction, 2005, 129:473-80 |
| centromere protein A, 17kDa; centromere protein E, 312kDa | CENPA, CENPE | A component of meiotic kinetochores required for meiosis I | Proc Natl Acad Sci USA, 1997, 94:9165-70; Chromosoma, 1988, 96:341-52 |
| BUB1 budding uninhibited by benzimidazoles 1 homolog beta (yeast) | BUB1B | Contribute to meiotic metaphase II arrest independent of spindle checkpoint activation | Reproduction, 2003, 126:443-50 |
| maternal embryonic leucine zipper kinase | MELK | May play a role in regulatory signal transduction pathways in oocyte | Mol Reprod Dev., 1997, 47:148-56 |
| BCL2-like 10 (apoptosis facilitator) | BCL2L10 | A component of the Bcl2 protein family important for the activation of a pro-apoptotic signalling pathway in ageing oocytes | Biol Reprod., 2005, [Epub ahead of print] |
| cyclin B1 | CCNB11 | Interacts with the cdc2 protein kinase to form the maturation promoting factor essential of oocyte maturation and arrest | Biol Reprod., 1997, 56:253-9 |
| cyclin A2 | CCNA2 | Distinct roles in both mitosis and meiosis based on expression and localization changes in oocytes from embryonic stages to post-natal and adult ovaries | Reproduction, 2005, 130:411-22 |
| aurora kinase B; aurora kinase C | AURKB, AURKC | Meiotic prophase I reactivation via the polyadenylation of specific transcripts such as Mos serine/threonine kinase | Biol Cell, 2004, 96:215-29 |
| DNA (cytosine-5-)-methyltransferase 1; DNA (cytosine-5-)-methyltransferase 3 beta | DNMT1, DNMT3b* | Maintenance methylation of imprinted alleles in oocyte and pre-implantation embryos | Dev Dyn., 2005, 232:992-1002; Dev Biol., 2002, 245:304-14; Mol Reprod Dev., 2002, 63:269-72 |

*DNMT3b is ranked within the top 200 genes

| Gene Symbol | Gene Title | FC (hOoc) | FC (hESC) |
|---|---|---|---|
| PDK1 | pyruvate dehydrogenase kinase, isoenzyme 1 | 65.81 | 6.96 |
| POU5F1 | POU domain, class 5, transcription factor 1 | 6.75 | 5.67 |
| JARID2 | Jumonji, AT rich interactive domain 2 | 48.31 | 5.05 |
| MSH2 | mutS homolog 2, colon cancer, nonpolyposis type 1 (E. coli) | 44.93 | 3.93 |
| DNMT3B | DNA (cytosine-5-)-methyltransferase 3 beta | 42.64 | 3.45 |
| PTTG1 | pituitary tumor-transforming 1 | 127.7 | 3.33 |
| CDT1 | DNA replication factor | 5.87 | 3.24 |
| KIF2C | kinesin family member 2C | 10.53 | 3.15 |
| BUB1 | BUB1 budding uninhibited by benzimidazoles 1 homolog (yeast) | 39.85 | 3.05 |
| ORC1L | origin recognition complex, subunit 1-like (yeast) | 37.76 | 2.99 |
| BIRC5 | baculoviral IAP repeat-containing 5 (survivin) | 3.09 | 2.92 |
| UNG | uracil-DNA glycosylase | 20.81 | 2.88 |
| CCNA2 | cyclin A2 | 224.87 | 2.77 |
| STK6 | serine/threonine kinase 6 | 188.96 | 2.76 |
| NASP | nuclear autoantigenic sperm protein (histone-binding) | 7.4 | 2.68 |
| CCNB1 | cyclin B1 | 138.32 | 2.66 |
| MCM7 | MCM7 minichromosome maintenance deficient 7 (S. cerevisiae) | 5.13 | 2.63 |
| CHEK1 | CHK1 checkpoint homolog (S. pombe) | 48.59 | 2.52 |
| CENPA | centromere protein A, 17kDa | 527.02 | 2.48 |
| PRIM2A | primase, polypeptide 2A, 58kDa | 8.9 | 2.42 |
| C10orf86 | chromosome 10 open reading frame 86 | 21.37 | 2.31 |
| EXOSC7 | exosome component 7 | 15.45 | 2.26 |
| AKAP1 | A kinase (PRKA) anchor protein 1 | 34.31 | 2.25 |
| CSPG6 | chondroitin sulfate proteoglycan 6 (bamacan) | 25.77 | 2.22 |
| MAD2L1 | MAD2 mitotic arrest deficient-like 1 (yeast) | 30.33 | 2.2 |
| CCNB2 | cyclin B2 | 204.76 | 2.19 |
| USP10 | ubiquitin specific peptidase 10 | 3.26 | 2.1 |
| PIAS2 | protein inhibitor of activated STAT, 2 | 5.2 | 2.09 |
| ASPM | asp (abnormal spindle)-like, microcephaly associated (Drosophila) | 836.86 | 2.08 |
| POLE2 | polymerase (DNA directed), epsilon 2 (p59 subunit) | 31.24 | 2.07 |
| TTK | TTK protein kinase | 194.33 | 2.07 |
| DNA2L | DNA2 DNA replication helicase 2-like (yeast) | 18.76 | 2.01 |
| ECT2 | epithelial cell transforming sequence 2 oncogene | 43.1 | 2 |
| MCM2 | MCM2 minichromosome maintenance deficient 2, mitotin (S. cerevisiae) | 71.22 | 1.98 |
| SNRPD1 | small nuclear ribonucleoprotein D1 polypeptide 16kDa | 5.2 | 1.97 |
| MCM10 | MCM10 minichromosome maintenance deficient 10 (S. cerevisiae) | 9.91 | 1.96 |
| NUP88 | nucleoporin 88kDa | 9.41 | 1.96 |
| NUP54 | nucleoporin 54kDa | 7.51 | 1.91 |
| CKS1B | CDC28 protein kinase regulatory subunit 1B | 27.18 | 1.88 |
| SAP30 | sin3-associated polypeptide, 30kDa | 9.71 | 1.87 |
| FLJ20364 | hypothetical protein FLJ20364 | 25.52 | 1.82 |
| SART3 | squamous cell carcinoma antigen recognised by T cells 3 | 15.78 | 1.82 |

| Gene | Description | Value 1 | Value 2 |
|---|---|---|---|
| HSPA14 | heat shock 70kDa protein 14 | 13.69 | 1.82 |
| HMGB2 | high-mobility group box 2 | 6.08 | 1.81 |
| DCLRE1A | DNA cross-link repair 1A (PSO2 homolog, S. cerevisiae) | 41.63 | 1.75 |
| TCL1A | T-cell leukemia/lymphoma 1A | 118.95 | 1.75 |
| RRM2 | ribonucleotide reductase M2 polypeptide | 73.43 | 1.75 |
| ASF1A | ASF1 anti-silencing function 1 homolog A (S. cerevisiae) | 56.65 | 1.75 |
| C14orf94 | chromosome 14 open reading frame 94 | 27.15 | 1.75 |
| GMNN | geminin, DNA replication inhibitor | 14.18 | 1.74 |
| PLK1 | polo-like kinase 1 (Drosophila) | 9.03 | 1.73 |
| FLJ11305 | hypothetical protein FLJ11305 | 25.08 | 1.71 |
| BLM | Bloom syndrome | 12.51 | 1.68 |
| SMN1 | survival of motor neuron 1, telomeric | 7.99 | 1.66 |
| CDCA3 | cell division cycle associated 3 | 27.59 | 1.65 |
| NUP93 | nucleoporin 93kDa | 11.92 | 1.63 |
| TRIP13 | thyroid hormone receptor interactor 13 | 43.14 | 1.55 |
| ORC6L | origin recognition complex, subunit 6 homolog-like (yeast) | 59.73 | 1.52 |
| NUP107 | nucleoporin 107kDa | 19.41 | 1.52 |
| TCOF1 | Treacher Collins-Franceschetti syndrome 1 | 21.64 | 1.51 |
| TCERG1 | transcription elongation regulator 1 | 3.71 | 1.51 |
| MCM4 | MCM4 minichromosome maintenance deficient 4 (S. cerevisiae) | 6.14 | 1.5 |
| NAP1L1 | nucleosome assembly protein 1-like 1 | 3.18 | 1.48 |
| MRPL18 | mitochondrial ribosomal protein L18 | 8.8 | 1.46 |
| DHFR | dihydrofolate reductase | 85.24 | 1.45 |
| MAPKAPK5 | mitogen-activated protein kinase-activated protein kinase 5 | 3.43 | 1.45 |

FIGURE 18

| GO Biological Process | No. of Genes | P Value | GO Molecular function | No. of Genes | P Value |
|---|---|---|---|---|---|
| Development | 249 | 1.88E-08 | Metal ion binding | 413 | 4.75E-06 |
| Cell proliferation | 86 | 4.57E-06 | RNA binding | 83 | 1.37E-05 |
| Cell differentiation | 80 | 1.47E-05 | GTPase regulator activity | 48 | 7.10E-05 |
| Nervous system development | 74 | 4.68E-05 | Hydrolase activity, acting on acid anhydrides | 83 | 3.65E-04 |
| System development | 74 | 6.15E-05 | Catalytic activity | 592 | 9.86E-04 |
| Cell communication | 400 | 6.53E-05 | Magnesium ion binding | 43 | 0.001518 |
| Cellular process | 1310 | 1.41E-04 | Enzyme regulator activity | 85 | 0.002361 |
| Regulation of cellular physiological process | 382 | 2.21E-04 | Calcium ion binding | 109 | 0.002456 |
| Signal transduction | 365 | 3.32E-04 | ATPase activity, coupled | 44 | 0.002512 |
| Organ development | 77 | 4.08E-04 | Transcription regulator activity | 158 | 0.002288 |

FIGURE 19(1)

| Gene Title | Gene Symbol | NCBI Accession No | Sequence |
|---|---|---|---|
| Homo sapiens protein arginine methyltransferase 5 (PRMT5), transcript variant 1 | PRMT5 | NM_006109 | GCGACTCGTCCCGCCTTCTGGGGCACTAGTTT GACTTTGTGATTGGCTACTAGTATCAAGGAAT CCCGGCGTGGACAGCGCGAGGAGAAAGATGGC GGCGATGGCGGTCGGGGGTGCTGGTGGGAGCC GCGTGTCCAGCGGGAGGGACCTGAATTGCGTC CCCGAAATAGCTGACACACTAGGGGCTGTGGC CAAGCAGGGGTTTGATTTCCTCTGCATGCCTG TCTTCCATCCGCGTTTCAAGAGGGAGTTCATT CAGGAACCTGCTAAGAATCGGCCCGGTCCCCA GACACGATCAGACCTACTGCTGTCAGGAAGGG ACTGGAATACGCTAATTGTGGGAAAGCTTTCT CCATGGATTCGTCCAGACTCAAAAGTGGAGAA GATTCGCAGGAACTCCGAGGCGGCCATGTTAC AGGAGCTGAATTTTGGTGCATATTTGGGTCTT CCAGCTTTCCTGCTGCCCCTTAATCAGGAAGA TAACACCAACCTGGCCAGAGTTTTGACCAACC ACATCCACACTGGCCATCACTCTTCCATGTTC TGGATGCGGGTACCCTTGGTGGCACCAGAGGA CCTGAGAGATGATATAATTGAGAATGCACCAA CTACACACACAGAGGAGTACAGTGGGGAGGAG AAAACGTGGATGTGGTGGCACAACTTCCGGAC TTTGTGTGACTATAGTAAGAGGATTGCAGTGG CTCTTGAAATTGGGGCTGACCTCCCATCTAAT CATGTCATTGATCGCTGGCTTGGGGAGCCCAT CAAAGCAGCCATTCTCCCCACTAGCATTTTCC TGACCAATAAGAAGGGATTTCCTGTTCTTTCT AAGATGCACCAGAGGCTCATCTTCCGGCTCCT CAAGTTGGAGGTGCAGTTCATCATCACAGGCA CCAACCACCACTCAGAGAAGGAGTTCTGCTCC TACCTCCAATACCTGGAATACTTAAGCCAGAA CCGTCCTCCACCTAATGCCTATGAACTCTTTG CCAAGGGCTATGAAGACTATCTGCAGTCCCCG CTTCAGCCACTGATGGACAATCTGGAATCTCA GACATATGAAGTGTTTGAAAAGGACCCCATCA AATACTCTCAGTACCAGCAGGCCATCTATAAA TGTCTGCTAGACCGAGTACCAGAAGAGGAGAA GGATACCAATGTCCAGGTACTGATGGTGCTGG GAGCAGGACGGGGACCCCTGGTGAACGCTTCC CTGCGGGCAGCCAAGCAGGCCGACCGGCGGAT AAAGCTGTATGCTGTGGAGAAAAACCCAAATG CCGTGGTGACGCTAGAGAACTGGCAGTTTGAA GAATGGGGAAGCCAAGTGACCGTAGTCTCATC AGACATGAGGGAATGGGTGGCTCCAGAGAAAG CAGACATCATTGTCAGTGAGCTTCTGGGCTCA |

FIGURE 19(2)

| | | | |
|---|---|---|---|
| | | | TTTGCTGACAATGAATTGTCGCCTGAGTGCCT<br>GGATGGAGCCCAGCACTTCCTAAAAGATGATG<br>GTGTGAGCATCCCCGGGGAGTACACTTCCTTT<br>CTGGCTCCCATCTCTTCCTCCAAGCTGTACAA<br>TGAGGTCCGAGCCTGTAGGGAGAAGGACCGTG<br>ACCCTGAGGCCCAGTTTGAGATGCCTTATGTG<br>GTACGGCTGCACAACTTCCACCAGCTCTCTGC<br>ACCCCAGCCCTGTTTCACCTTCAGCCATCCCA<br>ACAGAGATCCTATGATTGACAACAACCGCTAT<br>TGCACCTTGGAATTTCCTGTGGAGGTGAACAC<br>AGTACTACATGGCTTTGCCGGCTACTTTGAGA<br>CTGTGCTTTATCAGGACATCACTCTGAGTATC<br>CGTCCAGAGACTCACTCTCCTGGGATGTTCTC<br>ATGGTTTCCCATCCTCTTCCCTATTAAGCAGC<br>CCATAACGGTACGTGAAGGCCAAACCATCTGT<br>GTGCGTTTCTGGCGATGCAGCAATTCCAAGAA<br>GGTGTGGTATGAGTGGGCTGTGACAGCACCAG<br>TCTGTTCTGCTATTCATAACCCCACAGGCCGC<br>TCATATACCATTGGCCTCTAGCCCTGCGTGCC<br>AAGTGTCCAGAGCCTTGGAAGCAGCTTCAGGT<br>TCTGCTCCTGTAGTACAGAAGGTGCAGTACAT<br>CTATGGGCTGTGATTCCCCTTGCCCATCAGAG<br>AGGAGCATTTCAATCTGCTTTCCTGCCTTACA<br>TCAAGGTGGGCAAGGGATTATAATTAATTGCA<br>GGGCTCAAGCCACCAATCTATGAAGACCTCAG<br>GCCAGGGGTGAGGAATTAGTGCTGGATTTGA<br>AGCTACGCACTCAGCCTCAAGAACTCCCTGGA<br>ATATCCCTGAGAACATGGGGTTTGAACGGATT<br>TTCAGCCTTTTTCTGTTCTTGTTTTGATGGTT<br>TTGTGTAAGAGGAAATACAAATAAAGTTATAG<br>CCCTTTACTGCACGACC |
| Homo sapiens protein arginine methyltransferase 5 (PRMT5),transcript variant 2 | PRMT5 | NM_001039619 | GCGACTCGTCCCGCCTTCTGGGGCACTAGT<br>TTGACTTTGTGATTGGCTACTAGTATCAAG<br>GAATCCCGGCGTGGACAGCGCGAGGAGAAA<br>GATGGCGGCGATGGCGGTCGGGGGTGCTGG<br>TGGGAGCCGCGTGTCCAGCGGGAGGGACCT<br>GAATTGCGTCCCCGAAATAGCTGACACACT<br>AGGGGCTGTGGCCAAGCAGGGGTGAGGGCC<br>GGACCTCCACGAGCGGAATGCGGGGTCCGA<br>ACTCGGGGACGGAGAAGGGCAGACTAGTCA<br>TCCCGGAGAAGCAGGGGTTTGATTTCCTCT<br>GCATGCCTGTCTTCCATCCGCGTTTCAAGA<br>GGGAGTTCATTCAGGAACCTGCTAAGAATC<br>GGCCCGGTCCCCAGACACGATCAGACCTAC |

FIGURE 19(3)

| | | | |
|---|---|---|---|
| | | | TGCTGTCAGGAAGGGACTGGAATACGCTAA |
| | | | TTGTGGGAAAGCTTTCTCCATGGATTCGTC |
| | | | CAGACTCAAAAGTGGAGAAGATTCGCAGGA |
| | | | ACTCCGAGGCGGCCATGTTACAGGAGCTGA |
| | | | ATTTTGGTGCATATTTGGGTCTTCCAGCTT |
| | | | TCCTGCTGCCCCTTAATCAGGAAGATAACA |
| | | | CCAACCTGGCCAGAGTTTTGACCAACCACA |
| | | | TCCACACTGGCCATCACTCTTCCATGTTCT |
| | | | GGATGCGGGTACCCTTGGTGGCACCAGAGG |
| | | | ACCTGAGAGATGATATAATTGAGAATGCAC |
| | | | CAACTACACACACAGAGGAGTACAGTGGGG |
| | | | AGGAGAAAACGTGGATGTGGTGGCACAACT |
| | | | TCCGGACTTTGTGTGACTATAGTAAGAGGA |
| | | | TTGCAGTGGCTCTTGAAATTGGGGCTGACC |
| | | | TCCCATCTAATCATGTCATTGATCGCTGGC |
| | | | TTGGGGAGCCCATCAAAGCAGCCATTCTCC |
| | | | CCACTAGCATTTTCCTGACCAATAAGAAGG |
| | | | GATTTCCTGTTCTTTCTAAGATGCACCAGA |
| | | | GGCTCATCTTCCGGCTCCTCAAGTTGGAGG |
| | | | TGCAGTTCATCATCACAGGCACCAACCACC |
| | | | ACTCAGAGAAGGAGTTCTGCTCCTACCTCC |
| | | | AATACCTGGAATACTTAAGCCAGAACCGTC |
| | | | CTCCACCTAATGCCTATGAACTCTTTGCCA |
| | | | AGGGCTATGAAGACTATCTGCAGTCCCCGC |
| | | | TTCAGCCACTGATGGACAATCTGGAATCTC |
| | | | AGACATATGAAGTGTTTGAAAAGGACCCCA |
| | | | TCAAATACTCTCAGTACCAGCAGGCCATCT |
| | | | ATAAATGTCTGCTAGACCGAGTACCAGAAG |
| | | | AGGAGAAGGATACCAATGTCCAGGTACTGA |
| | | | TGGTGCTGGGAGCAGGACGGGGACCCCTGG |
| | | | TGAACGCTTCCCTGCGGGCAGCCAAGCAGG |
| | | | CCGACCGGCGGATAAAGCTGTATGCTGTGG |
| | | | AGAAAAACCCAAATGCCGTGGTGACGCTAG |
| | | | AGAACTGGCAGTTTGAAGAATGGGGAAGCC |
| | | | AAGTGACCGTAGTCTCATCAGACATGAGGG |
| | | | AATGGGTGGCTCCAGAGAAAGCAGACATCA |
| | | | TTGTCAGTGAGCTTCTGGGCTCATTTGCTG |
| | | | ACAATGAATTGTCGCCTGAGTGCCTGGATG |
| | | | GAGCCCAGCACTTCCTAAAAGATGATGGTG |
| | | | TGAGCATCCCCGGGGAGTACACTTCCTTTC |
| | | | TGGCTCCCATCTCTTCCTCCAAGCTGTACA |
| | | | ATGAGGTCCGAGCCTGTAGGGAGAAGGACC |
| | | | GTGACCCTGAGGCCCAGTTTGAGATGCCTT |
| | | | ATGTGGTACGGCTGCACAACTTCCACCAGC |

FIGURE 19(4)

| | | | |
|---|---|---|---|
| | | | TCTCTGCACCCCAGCCCTGTTTCACCTTCA GCCATCCCAACAGAGATCCTATGATTGACA ACAACCGCTATTGCACCTTGGAATTTCCTG TGGAGGTGAACACAGTACTACATGGCTTTG CCGGCTACTTTGAGACTGTGCTTTATCAGG ACATCACTCTGAGTATCCGTCCAGAGACTC ACTCTCCTGGGATGTTCTCATGGTTTCCCA TCCTCTTCCCTATTAAGCAGCCCATAACGG TACGTGAAGGCCAAACCATCTGTGTGCGTT TCTGGCGATGCAGCAATTCCAAGAAGGTGT GGTATGAGTGGGCTGTGACAGCACCAGTCT GTTCTGCTATTCATAACCCCACAGGCCGCT CATATACCATTGGCCTCTAGCCCTGCGTGC CAAGTGTCCAGAGCCTTGGAAGCAGCTTCA GGTTCTGCTCCTGTAGTACAGAAGGTGCAG TACATCTATGGGCTGTGATTCCCCTTGCCC ATCAGAGAGGAGCATTTCAATCTGCTTTCC TGCCTTACATCAAGGTGGGCAAGGGATTAT AATTAATTGCAGGGCTCAAGCCACCAATCT ATGAAGACCTCAGGCAGGGGTGAGGAAT TAGTGCTGGATTTGAAGCTACGCACTCAGC CTCAAGAACTCCCTGGAATATCCCTGAGAA CATGGGGTTTGAACGGATTTTCAGCCTTTT TCTGTTCTTGTTTTGATGGTTTTGTGTAAG AGGAAATACAAATAAAGTTATAGCCCTTTA CTGCACGACC |
| Homo sapiens cDNA clone IMAGE:5299642 | | BC041913 | TAATTCAGAATTGAGTAAAGAAATATTTTTC TAGTCCTTCATATATTGAAAACTTGCCACATG ACATTGTATCGTCTTCATTTTCCAGAAGATGC GTTGGTGTGCCATAGGTTTCTAACTTCCTTGA AAATAGTTTTTTAAGTCAATTGTAAATATACG TATTATTGTTAAAAGTAACTTTAAACTGCAAC ACATAGCTTCAAAACAATATAGAGATTTTGTA ATACCTTATAAGTGGAGTTGGCTAAAATACCT TATCCATATAAAACTTATTCTATTCTTTGCAT GCTTATTTTGTGTGTTGGTTGCTAGCTTAAAG TTTGATTTGTTGTTACTCTTTGTGTGCCAAAT TCACTAGGCAAGCGGATTTTTCCTCAGACTTC AAAAAATAATTCTTTTAAGAAAAAATGTAAAA ATGTTTATTCTAAAAAGCTGCATTAAAGGGAC AACCTATAAAAAGTTTTGCTAGCTCATCTTTA GAAGGAAGAAAGAATATTAGCTTGGGTGATGT TTAATTTGGGTGGCGATAGTTTCTGTAGGCTA AACTTTATGAGAAAAGTGTACCTACTCTATAA |

FIGURE 19(5)

| | | | |
|---|---|---|---|
| | | | AGGTAATAAATGTAAAACCTCTTGCTGTTATT GAGGAAGCTCTTCAACTACCCTAAATTTCACA AATGTAACTTATAACACTATGAAAAGATTTGA CCAACAATTTACGTTTGCTGTGTGCTTTAGTT TTTGTTTAAGCATATTCTTTTGCTTGAATTTC TGTGTTCATGAGAGTTAGGGTGTTTTATGCTT CTTGAACTAATTTTATAACATATTTAATATAT TACCAGTTAAGATATAAAATCATTTGTACATA GCGAATTGTAAAGCAGCTATTAAAGTAGGTGA AATAAAGTATATATTTGCCGGTTATCCATATC TTTTAGAAGTCCTGACAGAACAACCAGTTTAT TTGCACATAGGTAGCTTCTGTTTGAAGGAAGG TAAAGTTATAAGGAAACTCAAATACTATAAGA TGTGTCAAGGTATTTCTCCAGAATTAATTGCA AAGCTAGTGCTGAAGGATTTTAATCAGCTTCT AAAATTTTCTTCTCAATAAGACATATGTTTTG ATTACTTAGGGAAGATTCCTCATTTTTATTTG CCCTTTATGCATTTAATCCACATGATAGGACA TTAAAAATTAATATAAAGAAAAATCGTGCTCA TACTGTACATCTATTTCTGTGCTTGGAACTAC TTGTTAATAGTTTTTATCGAAGCTGTCAGCAA TAAGGGACATAAAACTGCTGTATTATACATTG TGGAATTGAATAAACAGCCTAATTTTTTTTT TCTAGTATAGGGTACTTAAGCATTTCCACTTT TGGAAGAAAAGTGTATTAGTATTTTATATTGC ATTTCATTTAAAAGGACAGTTTTTTTTTTTT TGTAAATCCATTCATTGAAATGGTTTCTAAAC TGTATAATGTAATTTGGAGCCTATTTAGTAAT AGAATTAAATGTCCTATGTAGTGCTACAATTT TTGAATTAGAAAGTGATCAAATGTAAGAAAAA AATTTAAAAATTCAGCCCAGAAAACAAAATAG TGTATTAAATTAGTTTAATGTAAAAGGAATTT ATAAGATTTTTTCCTCAATATAGATACCTCA CTTGAAAAGAAAGCACAGCATACTTAAAGTAG TTCTAGTAAACATGTCCTAGAAAACAGTTGCT AAATGTAGGACATCTTTTGAGGAATTAGTTTA TGAGAAATAAAATTTTACTTGTTTTTACTATC CTGTTAGAAGTATTTGTTTATCCTGATAATTT TAAGCCAACATAGTAGTCTTAAATTACTTTTG AATTTCTAATCTGTGAAGGCAGTAAATGAAAT ATCTGTTCTGCAACTGTTGAAACAAATAATTG GCTACATTGACCATAATTAAAGTTAAAATTTT GCCAATGATGTACAGTTTTATGGTTAAAGTTG CTGTGGTTGGTTGCATTACATGACACAGAAAA |

FIGURE 19(6)

| | | | |
|---|---|---|---|
| | | | CTGTCCTCTACCTCACGTGAAATAAATATTTT ATATGGTTTTACTAAAAATAAGACTCATGTAT CTGGTCACCTAGTTTACAAATTTTGAATTATA TTTATTGAAACATGACATACTGTGCTCTGAGC TTATACCTCAATTGTATTTTGTGCTGTTTTCC ATTTTCATGCCTTGTAAATAACTTGTATAGAT TGTGGATCAAATACTAAATAAAAACTTTTAAT GCCAAAAAAAAAAAAAAAA |
| Homo sapiens BTG family, member 2 (BTG2) | BTG2 | NM_006763 | CAGGGTAACGCTGTCTTGTGGACCCGCACT TCCCACCCGAGACCTCTCACTGAGCCCGAG CCGCGCGCGACATGAGCCACGGGAAGGGAA CCGACATGCTCCCGGAGATCGCCGCCGCCG TGGGCTTCCTCTCCAGCCTCCTGAGGACCC GGGGCTGCGTGAGCGAGCAGAGGCTTAAGG TCTTCAGCGGGGCGCTCCAGGAGGCACTCA CAGAGCACTACAAACACCACTGGTTTCCCG AAAAGCCGTCCAAGGGCTCCGGCTACCGCT GCATTCGCATCAACCACAAGATGGACCCCA TCATCAGCAGGGTGGCCAGCCAGATCGGAC TCAGCCAGCCCCAGCTGCACCAGCTGCTGC CCAGCGAGCTGACCCTGTGGGTGGACCCCT ATGAGGTGTCCTACCGCATTGGGGAGGACG GCTCCATCTGCGTCTTGTACGAGGAGGCCC CACTGGCCGCCTCCTGTGGGCTCCTCACCT GCAAGAACCAAGTGCTGCTGGGCCGGAGCA GCCCCTCCAAGAACTACGTGATGGCAGTCT CCAGCTAGGCCCTTCCGCCCCCGCCCTGGG CGCCGCCGTGCTCATGCTGCCGTGACAACA GGCCACCACATACCTCAACCTGGGGAACTG TATTTTTAAATGAAGAGCTATTTATATATA TTATTTTTTTTAAGAAAGGAGGAAAAGAA ACCAAAAGTTTTTTTTAAGAAAAAAAATCC TTCAAGGGAGCTGCTTGGAAGTGGCCTCCC CAGGTGCCTTTGGAGAGAACTGTTGCGTGC TTGAGTCTGTGAGCCAGTGTCTGCCTATAG GAGGGGGAGCTGTTAGGGGGTAGACCTAGC CAAGGAGAAGTGGGAGACGTTTGGCTAGCA CCCCAGGAAGATGTGAGAGGGAGCAAGCAA GGTTAGCAACTGTGAACAGAGAGGTCGGGA TTTGCCCTGGGGGAGGAAGAGAGGCCAAGT TCAGAGCTCTCTGTCTCCCCCAGCCAGACA CCTGCATCCCTGGCTCCTCTATTACTCAGG GGCATTCATGCCTGGACTTAAACAATACTA TGTTATCTTTTCTTTTATTTTTCTAATGAG |

FIGURE 19(7)

```
GTCCTGGGCAGAGAGTGAAAAGGCCTCTCC
TGATTCCTACTGTCCTAAGCTGCTTTTCTT
GAAATCATGACTTGTTTCTAATTCTACCCT
CAGGGGCCTGTAGATGTTGCTTTCCAGCCA
GGAATCTAAAGCTTTGGGTTTTCTGAGGGG
GGGGAGGAGGGAACTGGAGGTTATTGGGGT
TAGGATGGAAGGGAACTCTGCACAAAACCT
TTGCTTTGCTAGTGCTGCTTTGTGTGTATG
TGTGGCAAATAATTTGGGGGTGATTTGCAA
TGAAATTTTGGGACCCAAAGAGTATCCACT
GGGGATGTTTTTTGGCCAAAACTCTTCCTT
TTGGAACCACATGAAAGTCTTGATGCTGCT
GCCATGATCCCTTTGAGAGGTGGCTCAAAA
GCTACAGGGAACTCCAGGTCCTTTATTACT
GCCTTCTTTTCAAAAGCACAACTCTCCTCT
AACCCTCCCCTCCCCCTTCCCTTCTGGTCG
GGTCATAGAGCTACCGTATTTTCTAGGACA
AGAGTTCTCAGTCACTGTGCAATATGCCCC
CTGGGTCCCAGGAGGGTCTGGAGGAAAACT
GGCTATCAGAACCTCCTGATGCCCTGGTGG
GCTTAGGGAACCATCTCTCCTGCTCTCCTT
GGGATGATGGCTGGCTAGTCAGCCTTGCAT
GTATTCCTTGGCTGAATGGGAGAGTGCCCC
ATGTTCTGCAAGACTACTTGGTATTCTTGT
AGGGCCGACACTAAATAAAAGCCAAACCTT
GGGCACTGTTTTTTCTCCCTGGTGCTCAGA
GCACCTGTGGGAAAGGTTGCTGTCTGTCTC
AGTACAATCCAAATTTGTCGTAGACTTGTG
CAATATATACTGTTGTGGGTTGGAGAAAAG
TGGAAAGCTACACTGGGAAGAAACTCCCTT
CCTTCAATTTCTCAGTGACATTGATGAGGG
GTCCTCAAAAGACCTCGAGTTTCCCAAACC
GAATCACCTTAAGAAGGACAGGGCTAGGGC
ATTTGGCCAGGATGGCCACCCTCCTGCTGT
TGCCCCTTAGTGAGGAATCTTCACCCCACT
TCCTCTACCCCCAGGTTCTCCTCCCCACAG
CCAGTCCCCTTTCCTGGATTTCTAAACTGC
TCAATTTTGACTCAAAGGTGCTATTTACCA
AACACTCTCCCTACCCATTCCTGCCAGCTC
TGCCTCCTTTTCAACTCTCCACATTTTGTA
TTGCCTTCCCAGACCTGCTTCCAGTCTTTA
TTGCTTTAAAGTTCACTTTGGGCCCACAGA
CCCAAGAGCTAATTTTCTGGTTTGTGGGTT
GAAACAAAGCTGTGAATCACTGCAGGCTGT
```

FIGURE 19(8)

| | | | |
|---|---|---|---|
| | | | GTTCTTGCATCTTGTCTGCAAACAGGTCCC TGCCTTTTTAGAAGCAGCCTCATGGTCTCA TGCTTAATCTTGTCTCTCTTCTCTTCTTTA TGATGTTCACTTTAAAAACAACAAAACCCC TGAGCTGGACTGTTGAGCAGGCCTGTCTCT CCTATTAAGTAAAAATAAATAGTAGTAGTA TGTTTGTAAGCTATTCTGACAGAAAAGACA AAGGTTACTAATTGTATGATAGTGTTTTTA TATGGAAGAATGTACAGCTTATGGACAAAT GTACACCTTTTTGTTACTTTAATAAAAATG TAGTAGGATAAAAAAAAA |

IDENTIFICATION OF GENES OR POLYPEPTIDES THE EXPRESSION OF WHICH CORRELATES TO FERTILITY, OVARIAN FUNCTION AND/OR FETAL/NEWBORN VIABILITY

CROSS REFERENCE TO RELATED APPLICATIONS

This application is a continuation in part of U.S. Ser. No. 11/437,797 filed on May 22, 2006, which is in turn a continuation-in-part of U.S. Ser. No. 11/091,883 filed on Mar. 29, 2005. This application further claims the benefit of provisional application No. 60/556,875 filed Mar. 29, 2004. All of these applications are incorporated herein by reference in their entirety.

SEQUENCE LISTING

The instant application contains a "lengthy" Sequence Listing which has been submitted via CD-R in lieu of a printed paper copy, and is hereby incorporated by reference in its entirety. Said CD-R, recorded on Jan. 15, 2007, are labeled CRF, "Copy 1" and "Copy 2", respectively, and each contains only one identical 1.62 MB file (67839435.APP).

FIELD OF THE INVENTION

The present invention provides genetic methods that provide for the identification of "pregnancy competent" oocytes, i.e., oocytes that when fertilized and transferred to a suitable uterine environment are capable of yielding a viable pregnancy. The present invention further provides genetic methods of identifying female subjects, preferably human females having impaired fertility function, e.g., as a result of impaired ovarian function, e.g., as a result of age (menopause) or an underlying disease condition or therapy.

Also, the invention provides methods of evaluating the efficacy of a putative fertility treatment based on its effect on the expression of specific genes.

Further, the invention identifies genes which are differentially expressed by cumulus cells that correlate to the pregnancy potential of oocytes that are associated therewith.

Further, the present invention provides an improved mRNA amplification protocol that is especially suited for gene expression profiling of biological samples of small quantity, such as cumulus or stem cell containing cell samples.

BACKGROUND OF THE INVENTION

Currently, there is no available genetic procedures for identifying whether a female subject produces oocytes that are "pregnancy competent", i.e., oocytes which when fertilized by natural or artificial means are capable of giving rise to embryos that in turn are capable of yielding viable offspring when transferred to an appropriate uterine environment. Rather, conventional fertility assessment methods assess fertility e.g., based on hormonal levels, visual inspection of numbers and quality of oocytes, surgical or non-invasive (MRI) inspection of the female reproduction system organs, and the like. Often, when a woman has a problem in producing a viable pregnancy after a prolonged duration, e.g., more than a year, the diagnosis may be an "unexplained" fertility problem and the woman advised to simply keep trying or to seek other options, e.g., adoption or surrogacy. Therefore, providing alternative and more predictive methods for identifying women with fertility problems would be highly desirable. Likewise, novel and improved methods for treating fertility problems would be highly desirable.

Still further, the identification of women with fertility problems, preferably earlier on than by current methods is desirable, as fertility problems may correlate to other health issues that preclude pregnancy, e.g., cancer, menopausal condition, hormonal dysfunction, ovarian cyst, or other underlying disease or health related problems.

BRIEF DESCRIPTION AND OBJECTS OF THE INVENTION

It is an object of the invention to provide a novel and improved method of detecting infertility problems and the genetic basis thereof It is a more specific object of the invention to provide a novel method of detecting female fertility or infertility which method comprises evaluating the capability of oocytes produced by said female to potentially give rise to a viable pregnancy upon fertilization and transferal into a suitable uterine environment, wherein said method involves detecting the levels of expression of specific ("pregnancy signature") genes or polypeptides encoded thereby by cells that are oocyte-associated, e.g., cumulus cells.

It is another specific object of the invention to provide a method of evaluating whether a subject produces oocytes capable of giving rise to a viable pregnancy comprising:

(i) measuring the expression levels of genes in a oocyte-associated cell, e.g., a cumulus cell, wherein said genes are expressed or not expressed at characteristic levels ("pregnancy signature") in cells associated with oocytes capable of yielding a viable pregnancy; and (ii) detecting the "pregnancy potential" of said oocytes based on the level of similarity of said gene expression pattern to said "pregnancy signature".

It is another specific object of the invention to identify a female subject putatively having a condition that inhibits or prevents pregnancy by detecting whether said subject produces oocytes associated with cells, e.g., cumulus cells, which do not express one or more genes in a manner characteristic of "pregnancy competent" oocytes; wherein said method comprises detecting the expression of said one or more "pregnancy signature" genes in at least one cell associated with an oocyte isolated from said female subject; and thereby identifying the subject as potentially having a health problem which prevents or precludes fertility based on an abnormal expression pattern of at least one of said "pregnancy signature" genes.

It is another object of the invention to provide a method of evaluating the efficacy of a female fertility treatment which comprises:

(i) treating a female subject putatively having a problem that prevents or inhibits her from having a "viable pregnancy" and (ii) isolating at least one oocyte from said female subject and cells associated therewith after said fertility treatment;

(iii) isolating at least one cell associated with said isolated oocyte, preferably a cumulus cell, and detecting the level of expression of at least one gene that is expressed at a characteristic level of expression in "pregnancy competent" oocytes; and (iv) determining the putative efficacy of said fertility treatment based on whether said gene is expressed at a level characteristic of "pregnancy competent" oocytes as a result of treatment.

It is another object of the invention to provide animal models for evaluating the efficacy of putative fertility treatments comprising identifying genes which are expressed at characteristic levels in cumulus cells associated with pregnancy competent oocytes of a non-human animal, e.g., a non-human primate; and assessing the efficacy of a putative fertility treatment in said non-human animal based on its effect on said gene expression levels, i.e., whether said treatment results in said gene expression levels better mimicking gene expression levels observed in cumulus cells associated with pregnancy competent oocytes, ("pregnancy signature").

It is another object of the invention to identify specific human genes that are differentially expressed by cumulus cells and other oocyte-associated cells and to assay the expression of one or more of such specific genes by cumulus or other oocyte-associated cells as an indicator of fertility and ovarian function.

It is another object of the invention to provide a novel mRNA amplification protocol especially suited for biological samples of small quantity that combines the use of specific primers, i.e., SMART II oligonucleotide (Clontech, CA) and T7-oligo(dT)24V promoter primers (Ambion, TX).

BRIEF DESCRIPTION OF THE FIGURES

FIGS. 1A-1C and 1D-1I depict schematically a genetic fertility testing method according to the invention. FIG. 1A shows a freshly ovulated egg containing a polar body, zona pellucida and cumulus cells. FIG. 1B shows the fertilization and transferal of this egg into a uterine environment. FIG. 1C shows the recovery of cumulus cells from the oocytes shown in 1A which are to be used for genetic testing. FIG. 1D-1I show the isolation of RNAs from said cumulus cells, microarray analysis of said RNAs, validation of 100 genes by real time RT-PCR, correlation of the levels of expression of said genes (upregulated or downregulated) to the ability of an oocyte to give rise to a viable pregnancy, and the use of this gene expression profile to identify a set of genes, the expression of which correlates to the capability of an oocyte to yield a viable pregnancy ("pregnancy signature")

FIG. 2 contains a flow chart of the CRL amplification protocol used in the present invention. Figure discloses SEQ ID NO: 517.

FIG. 5 contains selected overrepresented GO biological processes in oocytes identified by EASE.

FIG. 7 contains primers and sequences used to validate RT-PCR microarray experimental results (SEQ ID NOS 518-537, respectively, in order or appearance).

FIG. 8 contains selected representations of genes common to human and mouse oocytes with homologs functionally characterized in the mouse oocyte (16 genes out of top 100 genes).

FIG. 9 contains 66 unique genes in common between human oocytes, mouse oocytes, hESCs, and mESCs.

FIG. 18 contains a Table containing the top 10 functional categories overreported in differentially expressed genes between cumulus cells coming from oocytes that produce progeny and those that fail to produce progeny. Gene orthology biological properties and molecular function as detected by EASE when oocyte expressed genes were compared to the genes represented in the GeneChip array.

FIG. 19 contains the sequences of three differentially expressed genes in FIG. 17 that are expressed on average at substantially elevated amounts in cumulus cells derived from occytes that give rise to progeny versus those which do not (SEQ ID NOS 538-541, respectively, in order or appearance).

DETAILED DESCRIPTION OF THE INVENTION

Figure 3:
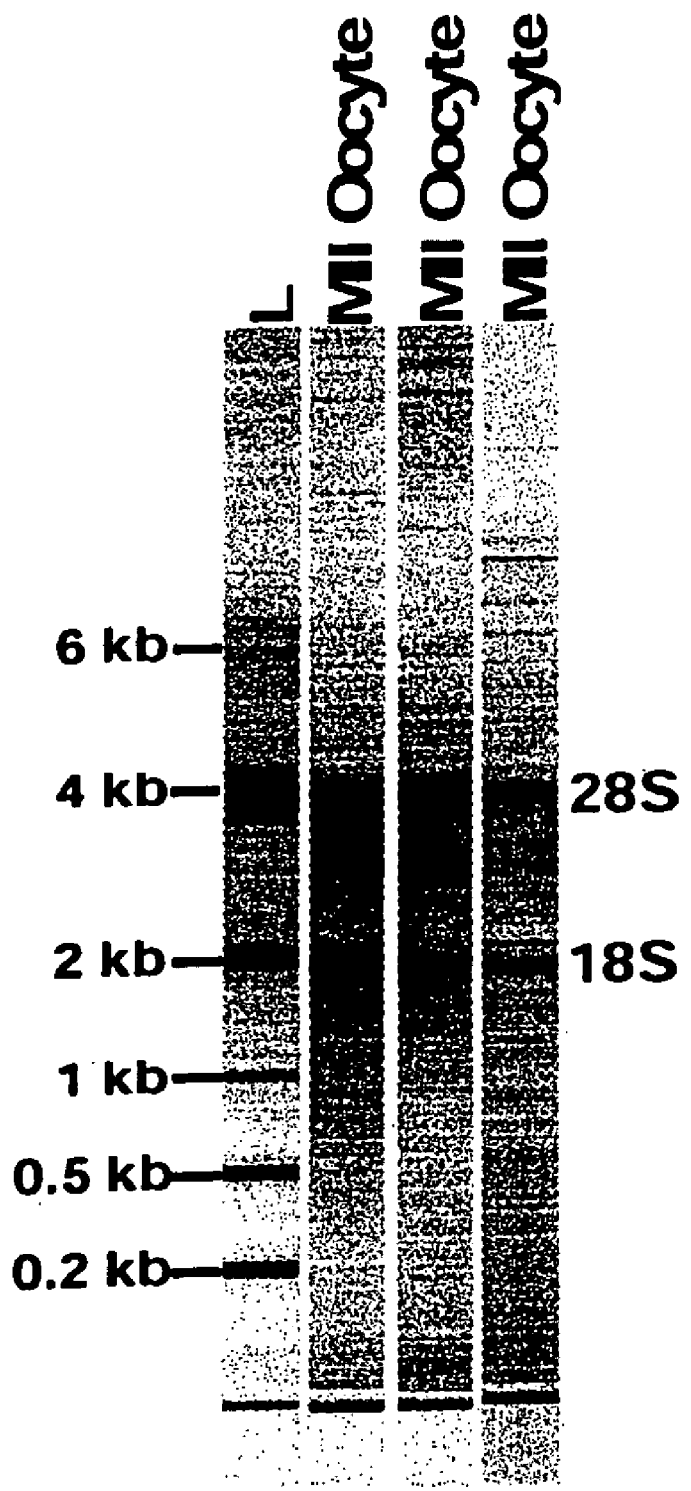
FIG. 3 contains a digital RNA gel-like image of total RNA sample isolated from 8 mature oocytes run 3 times.

Prior to discussing the invention in more detail, the following definitions are provided. Otherwise all words and phrases in this application are to be construed by their ordinary meaning, as they would be interpreted by an ordinary skilled artisan within the context of the invention.

"Pregnancy-competent oocytes": refers to a female gamete or egg that when fertilized by natural or artificial means is capable of yielding a viable pregnancy when it is comprised in a suitable uterine environment.

"Viable-pregnancy": refers to the development of a fertilized oocyte when contained in a suitable uterine environment and its development into a viable fetus, which in turn develops into a viable offspring absent a procedure or event that terminates said pregnancy.

"Cumulus cell" refers to a cell comprised in a mass of cells that surrounds an oocyte. This is an example of an "oocyte associated cell". These cells are believed to be involved in providing an oocyte some of its nutritional and or other requirements that are necessary to yield an oocyte which upon fertilization is "pregnancy competent".

"Differential gene expression" refer to genes the expression of which varies within a tissue of interest; herein preferably a cell from an oocyte, e.g., a cumulus cell.

"Real Time RT-PCR": refers to a method or device used therein that allows for the simultaneous amplification and quantification of specific RNA transcripts in a sample.

"Microarray analysis": refers to the quantification of the expression levels of specific genes in a particular sample, e.g., tissue or cell sample.

"Pregnancy signature": refers to a phrase coined by the inventors which refers to the characteristics levels of expression of a set of one or more genes, preferably at least 5, more preferably at least 10 to 20 genes, and still more preferably, at least 50 to 100 genes, that are expressed at characteristic levels in oocyte cells, preferably cumulus cells, that surround "pregnancy competent" oocytes. This is intended to encompass the level at which the gene is expressed and the distribution of gene expression within cells analyzed.

"Pregnancy signature gene": refers to a gene which is expressed at characteristic levels by a cell, e.g., cumulus cell, on a "pregnancy competent" oocyte.

"IVF": refers to in vitro fertilization.

"Zona pellucida" refers to the outermost region of an oocyte.

"Method for detecting differential expressed genes" encompasses any known method for evaluating differential gene expression. Examples include indexing differential display reverse transcription polymerase chain reaction (DDRT-PCR; Mahadeva et al., 1998, J. Mol. Biol. 284:1391-1318; WO 94/01582; subtractive mRNA hybridization (See Advanced Mol. Biol.; R. M. Twyman (1999) Bios Scientific Publishers, Oxford, p. 334, the use of nucleic acid arrays or microarrays (see Nature Genetics, 1999, vol. 21, Suppl. 1061) and the serial analysis of gene expression. (SAGE) See e.g., Valculesev et al., Science (1995) 270: 484-487) and real time PCR (RT-PCR). For example, differential levels of a transcribed gene in an oocyte cell can be detected by use of Northern blotting, and/or RT-PCR.

CRL amplification protocol refers to the novel total RNA amplification protocol depicted schematically in FIG. 2 that combines template-switching PCR and T7 based amplification methods. As noted above, this protocol is well suited for samples wherein only a few cells or limited total RNA is available.

Preferably, the "pregnancy signature" genes will be detected by hybridization of RNA or DNA to DNA chips, e.g., filter arrays comprising cDNA sequences or glass chips containing cDNA or in situ synthesized oligonucleotide sequences. Filtered arrays are typically better for high and medium abundance genes DNA chips can detect low abundance genes. In the exemplary embodiment the sample may be probed with Affymetrix GeneChips comprising genes from the human genome or a subset thereof.

Alternatively, polypeptide arrays comprising the polypeptides encoded by pregnancy signature genes or antibodies that bind thereto may be produced and used for detection and diagnosis.

"EASE" is a gene ontology protocol that from a list of genes forms subgroups based on functional categories assigned to each gene based on the probability of seeing the number of subgroup genes within a category given the frequency of genes from that category appearing on the microarray.

As noted above, the present invention preferably provides a novel method of detecting whether a female subject, human or non-human, produces "pregnancy competent" oocytes. The method involves detecting the levels of expression of one or more genes that are expressed or not expressed at characteristic levels by cumulus cells associated with (surrounding) oocytes that are "pregnancy competent", i.e., which when fertilized by natural or artificial means (IVF), and transferred into a suitable uterine environment are capable of yielding a viable pregnancy, i.e., embryo that develops into a viable fetus and eventually an offspring unless the pregnancy is terminated by some event or procedure, e.g., a surgical or hormonal intervention.

The invention further provides a novel and improved means for amplifying the total RNA from a particular cell sample that combines template-switching PCR and T7-based amplification methods (referred to herein as CRL amplification protocol). While this method is preferably used for assaying gene expression by oocyte, cumulus, or ES total RNA samples it is applicable for any cell sample, preferably a cell sample wherein amplifiable RNA is only available in small quantity.

The invention further provides transcriptome data obtained from oocyte, cumulus, or ES cells that identifies genes which are differentially expressed therein.

The invention in particular identifies 1626 genes that are differentially expressed by human ES cells.

The invention further identifies 5331 transcripts upregulated and 7074 transcripts down-regulated in human oocyte sample. Upregulated genes include FIGLA, STELLA, VASA, DAZL, GDF9, ZP1, ZP2, MOS, OCT4, NPM2, and H1FOO.

The invention further compares transcriptomes from human and mouse oocytes and identifies 1587 genes common (differentially expressed) to both.

The invention further compares the transcriptomes of oocytes and ES cells and identifies 388 (human) and 591 (mouse) genes differentially expressed in both as well as a set of 66 genes that are preferentially differentially expressed in each of human and mouse ESCs and oocytes.

In particular the invention provides a comprehensive expression baseline of gene transcripts present in in vivo matured metaphase II human oocytes.

In preferred embodiments, the inventive methods will be used to identify women subjects who produce or do not produce pregnancy competent oocytes based on the levels of expression of a set of differentially expressed genes. However, the inventive methods are applicable to non-human animals as well, e.g., other mammals, avians, amphibians, reptiles, et al. For example, the subject invention may be used to derive animal models for the study of putative female fertility treatments.

Additionally, the present invention may be used to identify female subjects who have an abnormality that precludes or inhibits their ability to produce pregnancy competent oocytes, e.g., ovarian dysfunction, ovarian cyst, pre-menopausal or menopausal condition, cancer, autoimmune disorder, hormonal dysfunction, cell proliferation disorder, or another health condition that inhibits or precludes the development of pregnancy competent oocytes.

For example, subjects who do not express specific pregnancy signature genes at characteristic expression levels will be screened to assess whether they have an underlying health condition that precludes them from producing pregnancy competent oocytes. Particularly, such subjects will be screened to assess whether they are exhibiting signs of menopause, whether they have a cancer, autoimmune disease or ovarian abnormality, e.g., ovarian cyst, or whether they have another health condition, e.g., hormonal disorder, allergic disorder, etc., that may preclude the development of "pregnancy competent" oocytes.

Additionally, the subject methods may be used to assess the efficacy of putative female fertility treatments in humans or non-human female subjects. Essentially, such methods will comprise treating a female subject, preferably a woman, with a putative fertility enhancing treatment, isolating at least one oocyte and associated surrounding cells from said woman after treatment, optionally further isolating at least one oocyte and associated surrounding cells prior to treatment, isolating at one cumulus cell from each of said isolated oocytes; detecting the levels of expression of at least one gene that is expressed or not expressed at characteristic levels by cumulus cells that are associated with (surround) pregnancy competent oocytes; and assessing the efficacy of said putative fertility treatment based on whether it results in cumulus cells that express at least one pregnancy signature gene at levels more characteristic of cumulus cells that surround pregnancy competent oocytes (than without treatment). As noted, while female human subjects are preferred, the subject methods may be used to assess the efficacy of putative fertility treatments in non-human female animals, e.g., female non-human primates or other suitable animal models for the evaluation of putative human fertility treatments.

Still further, the present invention may be used to enhance the efficacy of in vitro or in vivo fertility treatments. Particularly, oocytes that are found to be "pregnancy incompetent", or are immature, may be cultured in a medium containing one or more gene products that are encoded by genes identified as being "pregnancy signature" genes, e.g., hormones, growth factors, differentiation factors, and the like, prior to, during, or after in vivo, or in vitro fertilization. Essentially, the presence of these gene products should supplement for a deficiency in nutritional gene products that are ordinarily expressed by cumulus cells that surround "pregnancy competent" oocytes, and which normally nurture oocytes and thereby facilitate the capability of these oocytes to yield viable pregnancies upon fertilization.

Alternatively, one or more gene products encoded by said pregnancy signature genes may be administered to a subject who is discovered not to produce pregnancy competent oocytes according to the methods of the invention. Such administration may be parenteral, e.g., by intravenous, intramuscular, subcutaneous injection or by oral or transdermal administration. Alternatively, these gene products may be administered locally to a target site, e.g., a female ovarian or uterine environment. For example, a female subject may have her uterus or ovary implanted with a drug delivery device that provides for the sustained delivery of one or more gene products encoded by "pregnancy signature" genes.

Also, the novel CRL amplification protocol of the invention may be used to identify differentially expressed genes from any cell sample, preferably those only available in limited numbers such as e.g., samples used in forensic analysis, pathological samples such as cancer cells, especially cancer stem cells, cell samples suspected of containing an unknown pathogen, cell samples obtained from cells undergoing specific cellular processes such as differentiation, apoptosis, angiogenesis, and the like. This protocol has been found to faithfully and consistently amplify small amounts of RNA to quantities required for microarray analysis.

Thus, in general, the present invention involves the identification and characterization, in terms of gene identity and relative abundance, of genes that are expressed by desired cells, e.g., cumulus cells derived from an egg, preferably human egg, at the time of ovulation, preferably cumulus cells, the expression levels of which correlate to the capability of said egg to give rise to a viable pregnancy upon natural or artificial fertilization and transferal to a suitable uterine environment. Also, the invention identifies a set of genes differentially expressed by human or murine ESCs and metaphase II oocytes.

In one preferred embodiment, of the invention at least 50 to 100 genes that are significantly upregulated or downregulated, by cumulus cells that correlate to the "pregnancy competency" of an oocyte from which said cumulus cells are associated with will be chosen and monitored in the inventive genetic testing methods.

However, while the invention preferably will select at least 50-100 genes from each of said categories, it is anticipated that the inventive methods alternatively may be practiced by monitoring the expression levels of fewer numbers of cumulus cell expressed genes, wherein said genes are similarly selected to be those which correlate to cumulus cells associated with "pregnancy competent" oocytes, i.e., those that are capable of yielding viable pregnancies.

According to the invention, gene expression levels will preferably be detected by the novel CRL amplification protocol provided herein. However other known methods, preferably real time detection methods such as mentioned above may be used to detect and quantify gene expression. Methods for detecting relative gene expression levels are known in the art and well within the purview of the ordinary skilled artisan.

As noted supra, this invention further provides a novel mRNA amplification protocol that is well suited for small cell samples such as those containing only a few or even a single cumulus cell or oocyte or ESC or other desired cells. This amplification protocol is well suited as well for forensic applications where only a minute nucleic acid sample may be available. Also, this technique is useful wherein only a few cells may be isolated from an individual such as adult stem cells, cancer stem cells, other differentiation specific cells, olfactory cells, taste cells, and the like. The present protocol will be useful in the biomedical field such as by medical and veterinary pathologists, e.g. in coordination with Laser-assisted Microdissection of tissues. Particularly, such applications may include cancer-related applications, research and disease diagnosis.

Previously, in order to generate a biotin-labeled antisense aRNA target for GeneChip experiments from limited amount of RNA samples, this entailed the use of commercial kits e.g., those available from a few venders (such as Ambion TX, and Arcturus, CA). All of these kits use the same approach based on the Eberwine T7 amplification method (See Eberwine Biotechniques 20:584-591 (1996)).

By contrast, the present invention provides an improvement thereover that faithfully and consistently amplifies small amounts of RNA to quantities required to perform microarray experiments. The CRL amplification protocol disclosed herein provides a practical approach to facilitate the analysis of gene expression in samples of small quantity while maintaining the relative gene expression profile throughout reactions (Kocabas et al., "Transcriptome Analysis of the Human Oocyte" In Press, 2006).

This amplification protocols achieves at least the following advantages versus available protocols:

(i) global mRNA amplification is possible for a limited number of cells, tissues and micro-dissected biopsy using other (non-CRL) PCR amplification method;

(ii) the protocol is comprised of simple laboratory manipulations;

(iii) the simplicity of the protocol contributes to a high level of reproducibility from experiment to experiment; and (iv) the protocol time is shorter than other methods, in particular when multiple rounds are performed.

Based on these advantages this methodology is well suited for use in the present differential gene expression based-assays which detect genes the expression of which correlates to oocytes or embryonic stem cells as well as other applications wherein the detection of expressed genes in a sample is desired.

Essentially, the CRL protocol is depicted in FIG. 2 and comprises (i) first strand cDNA synthesis coupled with dC tailing by MMLV RT (Rnase H-); (ii) template switching and chain extension by RT; (iii) amplification of cDNA a requisite number of cycles, typically 5 to 50, more preferably around 10-20, more preferably around 15 cycles by LD-PCR using SMART primers; (iv) and production of double stranded DNAs by in vitro transcription using T7 RNA polymerase. As noted this methodology is applicable for amplification of mRNAs in any sample, but preferably is used in amplifying mRNAs from relatively small cell samples such as samples containing a few number of cumulus cells, oocytes, or stem cells.

In the inventive pregnancy signature gene detection methods, cumulus cells will be isolated from oocytes of different female subjects, the oocytes fertilized by known IVF procedures, and the cumulus cells of the corresponding isolated oocytes being subjected to gene expression analysis, i.e., by isolation of total RNA therefrom, amplification of said total RNA, quantification of the relative gene expression levels of said RNAs by microarray analysis and RT-PCR, and the identification of genes, the expression of which correlates to oocytes that give rise to a viable pregnancy.

To effect such identification, as a separate step, the status of embryos fertilized with oocytes derived from each of said cumulus cell samples will be monitored and pregnancy data recorded. Particularly, the relative birth rate and the health status of the newborn for each oocyte will be recorded and the gene expression levels of cumulus cells associated with each oocyte assessed as a function of pregnancy rate, newborn health, among other parameters, e.g., gender. Based on these results, a set of genes the expression of which correlates to pregnancy/health outcome or gender will be identified. ("pregnancy signature").

This set of genes, and the corresponding expression levels is referred to herein as the "pregnancy signature" because these gene expression levels correlate to the development of a viable pregnancy and ultimately the production of a healthy newborn. While this "pregnancy signature" may comprise as many as 50, 100 or even 200 genes, it is anticipated that a fewer number of genes, e.g., on the order of 20 or less genes, may be sufficient to develop a suitable "pregnancy signature".

The genes which constitute the "pregnancy signature" may include genes which encode gene products that are involved in the nutritional and developmental requirements of the oocyte, i.e., maturation and development, and the potential of the oocyte to be capable of yielding a viable pregnancy. These gene products may include growth factors, hormones, transcription factors, differentiation promoting agents, and the like. After the "pregnancy signature" is obtained, the corresponding genes are sequenced, the DNA sequences are then used to deduce the identify the corresponding polypeptide sequences, and these sequences then compared to databases of available human or other gene sequences to identify the identity of the gene products that correlate to the ability of an oocyte to yield a viable pregnancy. Genes which are differentially expressed by human oocytes are identified infra and include such pregnancy signature genes. Further statistical analysis of the relative levels of expression of these genes, or subsets of such genes, will identify preferred subsets of these genes that constitute a "pregnancy signature" of a viable oocyte, i.e., one that is pregnancy competent. Some genes found to be differentially expressed in cumulus cells are contained in SEQ ID NO's 1-513 infra. Additionally, FIG. 19 contains the sequences of three genes which are differentially expressed and expressed at different levels in human cumulus cells associated with oocytes that give rise to viable pregnancies versus cumulus cells associated with oocytes that do not give rise to viable pregnancies. These three genes are the human arginine methyltransferase gene (PRMT5) and its transcript variants and other allelic variants, the human gene identified in FIG. 19 as Clone IMAGE 5299642 and contained in deposited NCBI Accession Sequence BC041913; ACTB, and human BTG family member, member 2, BTG2, and contained in deposited NCBI Accession Sequence NM_006763. The results of the gene expression experiments contained in Example 3 suggest that these 3 genes are all expressed at detectably higher amounts in cumulus cells that are associated with oocytes that give rise to viable pregnancies versus those that do not. While the expression results are qualitative and have not yet been quantified the qualitative results would reasonably suggest that these genes are all expressed at levels which are least 2-3 fold greater in cumulus cells associated with oocytes that give rise to viable pregnancies, and likely up to 5-10-fold greater. Therefore, detecting the expression of these genes by cumulus cells derived from different donor oocytes, e.g., those to be used in an IVF procedure may be used as one means of predicting the pregnancy potential of the oocytes associated therewith, i.e., cumulus cells with higher levels of expression of these genes are more likely to be associated with oocytes useful in IVF procedures. Therefore, these genes may be used as part of the pregnancy signature set of genes the expression of which is assayed in order to assess the pregnancy potential of oocytes from a donor, e.g., a patient who is contemplating being an IVF donor. Also, these gene expression procedures may be used to assess the pregnancy potential of oocytes in an individual who is undergoing fertility treatments, an individual who is near menopause (perimenopause), or an individual who has or had a disease or condition or treatment that potentially would impact the viability and quality of her oocytes such as radiation or chemotherapy.

As noted previously, these polypeptide gene products which are found to be deficient in pregnancy incompetent oocytes may be added to in vitro culture media containing oocytes in order to enhance their pregnancy competency or alternatively may be administered in vivo as part of a fertility treatment regimen.

EXAMPLE 1

Exemplification of CRL Amplification Protocol of the Invention with Oocyte and ES Cell Samples Oocyte Collection, Total RNA Extraction and Reference RNA Human oocytes were obtained from 3 patients undergoing an assisted reproductive treatment (ART) at the unit of Reproductive Medicine at Clinica Las Condes, Santiago Chile. The selection criteria for the donors was a) less than 35 years old, (b) reproductively healthy with regular ovulatory cycles; (c) male factor as the only cause of infertility , (d) considerable number of developing follicles that assured spared oocytes. The experimental protocol was reviewed and approved by a local independent Ethics Review Board. All donors signed informed consent. At the time of this application filing, all three donors has already conceived, two of them got pregnant during the ART cycle in which the samples were collected, and the third one got pregnant following a spontaneous cycle with artificial insemination using donated sperm. Ovarian stimulastion and oocyte retrieval and isolation were performed as described herein.

Three groups of 10 oocytes were used. Total RNA was isolated following the guanidium thiocyanate method (28) using the PicoPure RNA isolation kit (Arcturus, CA) following manufacturer's instructions except only 6.6 micromolar elution buffer was used and the elution was repeated at least 3 times using the first eluate. All RNA samples within the purification column were treated with the Rnase-Free Dnase (Qiagen, CA). Extracted RNA was stored at −80 degrees C. until used as a template for cDNA synthesis. The quality and quantity of extracted total RNA from 8 matured oocytes (independent from the 30 oocytes used in this experimental study (was evaluated using the Agilent 2100 bioanalyzer (Agilent Technologies, CA). Each mature oocyte was found to have about 330 pg total RNA when the Arcturus' RNA isolation kit was used. Quality of RNA was intact as shown in FIG. 3. Reference RNA (100 micrograms) was prepared by mixing 10 micrograms total RNA from each of 10 different normal human tissues including skeletal muscle, kidney, lung, colon, liver, spleen, breast, brain, heart and stomach (Ambion, TX).

RNA Amplification for GeneChip Analysis (FIG. 4a)

First-strand cDNA synthesis: the following reagents were addded to each of 0.5 ml Rnase-free tube: 5 micromolar total RNA (3 ng for the reference and5 microliters, about 3 ng, for the oocyte samples) and 300 ng of an anchored T7-Oligo(dT) 24 V promoter primer (Ambion TX). The reaction tubes were incubated in preheated PCR machine at 70 degreees C. for 2 min and transferred to ice. After denaturation, trhe following reagents were added to each tube: 1.4 microliters of SMART II A oligonucleotide (5'-AAGCAGTGGTATCAACGCA-GAGTACGCGrGrGr-3") (SEQ ID NO: 514) (Clonetech, CA), 4 microliters of 5× first-strand buffer, 2 microliters of 20 mm DTT, 0.6 microliters of 5 mg/ml T4 Gene 32 Protein (Roche, IN), 2 microliters of 10 mM dNTPs, 20 U Rnase inhibitor (Ambion, TX) and 1 microliter PowerScript Reverse Trasnscriptase (Clontech, CA). After gentle mixing, reaction tubes were incubated at 42 degrees C. for 60 minutes in a hot-lid thermal cycler. The reaction was terminated by heating at 70 degrees C. for 15 minutes and purified by NucleoSpin Extraction Kit (Clontech, CA).

Double-stranded cDNA synthesis by Long-distance (LD)-PCR, cDNA purification: PCR Advantage 2 mix (9 microliters) was prepared as follows: 5 microliters of 10× PCR Advantage buffer (Clontech, CA), 1 microliter of 10 mM dNTPs, 100 ng 5' SMART upper primer (5'-AAGCAGTGG-TATCAACGCAGAGTA-3') (SEQ ID NO: 515), 100 ng 3' SMART lower primer (5'-CGGTAATACGACTCACTAT-AGGGAGAA-3') (SEQ ID NO: 516), and 1 microliter of Polymerase Mix Advantage 2 (clontech, CA). This mix was added to 41 microliters of the first-strand cFDNA synthesis product, and thermal cycling was carriedout in the following conditions: 95 degrees C. for 1 minute, folowed by 15 cycles, each consisting of denaturation at 94 degrees C. for 30 sec, annealing at 62 degrees for 30 sec, and extension at 68 degrees C. for 10 min. The cDNA was purified by NucleoSpin Extraction Kit following the manufacturer's insructions.

In vitro transcription (IVT), biotin labeled aRNA purification and aRNA fragmentation is described herein.

Microarray Analysis: Transcription profile of each sample was probed using Affymetrix Human Genome U133 Plus 2.0 GeneChips. The raw data obtained after scanning the arrays was analyzed by dChip (29). A smoothing spline normalization method was applied prior to obtaining model-based gene expression indices, a.k.a. signal values. There were no outliers identified by dChip so all samples were carried on for subsequent analysis.

Pathway analysis was performed using Ingenuity Software Knowledge Base (Redwood City, Calif.) which is a manually created database of previously published findings on mammalian biology from the public literature. We used the network analysis using the knowledge base to identify interactions of input genes within the context of known biological pathways.

Gene ontology (GO) was performed using EASE. Given a list of genes, EASE forms subgroups based on the functional categories assigned to each gene. EASE assigns a significance level (EASE score) to the functional category based on the probability of seeing the number of subgroup genes within a category given the frequency of genes from that category appearing on that microarray (30)

Comparison with External Data Sets

Mouse MII oocyte transcriptome data was obtained from Su et al., who used custom designed Affymetrix chips to obtain gene expression profiles of oocytes and 60 other mouse tissue types. (31) Using their expression database we identified 3,617 differentially upregulated transcripts in the mouse oocyte by using the median expression value of the remaining 60 samples as the baseline (Supplementary dataset 1, not. shown). We selected transcripts with an expression value in oocyte samples that are 2-fold higher than the base-line.

Human embryonic stem cell (hESC) data was derived from the work of Sato et al. who profiled human stem cells and their differentiated counterparts using Affymetrix HG-U133A representing around 2200 transcripts. (32)

We analyzed raw data using dChip and identified 1,626 hESC genes by selecting transcripts significantly upregulated in human stem cells compared to their differentiated counterparts (Supplementary dataset 2, not shown).

Finally for mouse ES cells we used a list of 1,687 differentially upregulated mouse ES genes published by Fortunel et al. (33) which were identified by comparing mouse ES cells to differentiated cells using Affymetrix MG-U74Av2 chips representing around 1200 transcripts (Supplementary dataset 3, not shown). We used Affymetrix' NetAffix tool for mapping genes across organisms and platforms used in the respective studies.

RESULTS AND CONCLUSIONS

Validation of Amplification Fidelity (Amplified vs. Non-Amplified RNA)

A critical step in the analysis of gene expression on small samples is the faithful amplification of mRNA molecules present in the sample. We have designed a PCR based amplification system using the combination of SMART UII A oligonucleotide (Clontech, CA) and T7-Oligo (dT) promoter primers ("CRL amplification protocol"). (FIG. 3a) We have isolated total RNA from a human cell line and 20, 3 and 1.5 ng input total RNA was amplified using CRL amplification protocol. For each experiment, 15 micrograms of fragmented aRNA was hybridized to a single Affymetrix Human Genome U133 Plus 2.0 array. Non-amplified RNA from the original sample (12 micrograms) was run in parallel by using the MessageAmp II aRNA Kit (Ambion, TX). Gene expression results from both amplified vs non-amplified RNA samples were compared and the correlation coefficients were found to be 0.94. (FIG. 3b), 0.03, and 0.91 respectively for 20 ng, 3 ng, and 1.5 ng of total input RNA respectively. CRL amplification protocol was repeated two times with 20 ng initial total RNA from the same cell type and the correlation between the two experiments was 0.99. These results show that the subject RNA amplification strategy faithfully and consistently amplifies even small amounts of RNA to quantities required to perform microarray experiments. The CRL amplification protocol provides a practical approach to facilitate the analysis of gene expression in samples of small quantity while maintaining the relative gene expression profile throughout reactions.

Differentially Upregulated Genes in the Human Oocyte

We generated a databases of the human oocyte transcriptome by comparing the transcripts in the oocyte and the reference samples which contain mRNA from several somatic tissues. A complete list of up and down regulated genes, functional comparative and correlation analysis is provided (see Supplementary dataset 4). Compared to reference samples there were 5,331 transcripts significantly up-regulated and 7,074 transcripts significantly down-regulated in the oocyte. Genes up-regulated in oocyte samples included most of the well-known germ cell specific genes, such as FLGLA, STELLA, VASA, DAZL, GDF9, ZP1, ZP2, MOS, OCT4, NPM2, and H1F00. (FIG. 4), Our analysis also confirms the presence of pathways previously described in the mouse, in particular the TGF-beta pathway (FIG. 5)

Validation of Microarray Data

Figure 4:
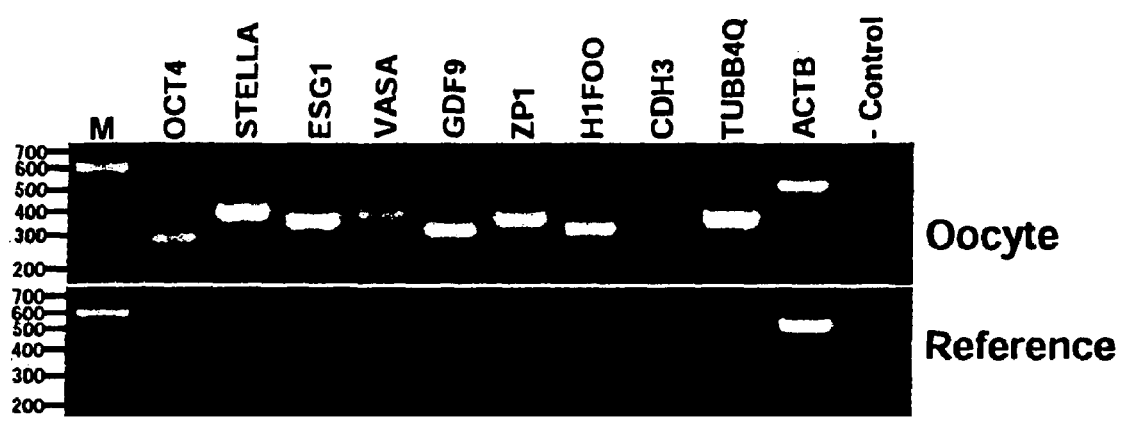
FIG. 4 contains RT-PCR verification of GeneChip array results for samples as described infra.

A selected list of genes known to be expressed in the oocyte was used to validate the microarray results by TR-PCR (FIG. 4). These genes were found to be present in the oocyte sample and absent in the reference RNA.

Functional Annotation of Genes Over-Expressed in the Human Oocyte

To examine the biological processes performed by the oocyte, we implemented EASE (36), contrasting the genes over-expressed in the oocyte with all the genes present in the Affymetrix chip (Table 1). One of the top over-represented categories found in oocytes was related to RNA metabolism. This is in agreement with the fact that oocytes store RNA to support the events of fertilization and early embryonic development until the embryonic gene is activated. (34, 35, 36) DNA metabolism and chromatin modification were also over-represented categories, in agreement with the need of the oocyte to remodel the sperm chromatin upon fertilization.

Cell cycle related categories were the most over-represented. Many genes known to be involved in the regulation of the meiotic cell cycle Many genes known to be involved in the regulation of the meiotic cell cycle were detected (MOS, AKT2, CDC25, and PLK1) (37) Detection of gametogenesis and reproduction as over-represented categories further suggests the accuracy of this transcriptional profiling. Protein kinases and phosphatases denoted another functional category over-represented in oocytes. Many of the cell cycle regulatory genes (AURKB, CDC25, DCD7, PLK1, CDC23 and plk3) and some receptors of the TGF superfamily (ACVR1, ACVR2B, and BMPR1A and 1B) were in this category.

An important category that is highly represented in thr oocyte was related to nucleic acid metabolism and regulation of transcription. Although transcriptionally silent at the MII stage, the oocyte is very active in transcription and translation during its growth phase and must be prepared to initiate transcription at the time of embryonic genome activation, 4- to 8-cell stage in human (38). Many of the genes in this category represent Zinc0-finger proteins that are not yet fully characterized, providing an opportunity to discover new transcriptional regulatory networks that operate during embryonic genome activation.

We also found that chromatin remodeling genes are well represented in the human oocyte. Genes in this category expressed in the human oocyte were: DNA methyltransferases (DNMT1, DNMT3a, and DNMT3B), histone acetyltransferases (NCOA1, and 3, SRCAP, GCN5L2 and TADA2L), histone deacetyltransferases (HDAC3 HDAC9, SIRT7), methyl-CpG-binding proteins (MBD2 and MBD4), histone methyltransferases (EHMT1 and SET8), ATP-dependent remodeling complexes (SMARCA1, SMARCA5, SMARCAD1, SMARCC2, SMARCD!) and other chromatin modifying genes (ESR1, NCOA6, HMGB3, HMGN1 and HMGA1).

These GO results validate our transcriptome analysis when compared with candidate gene analysis already reported in other species but more importantly, shed new light into a large number of biological processes that take place in the human oocyte.

Intersection between Human Oocyte and Mouse Oocyte Transcriptome

Figure 6:
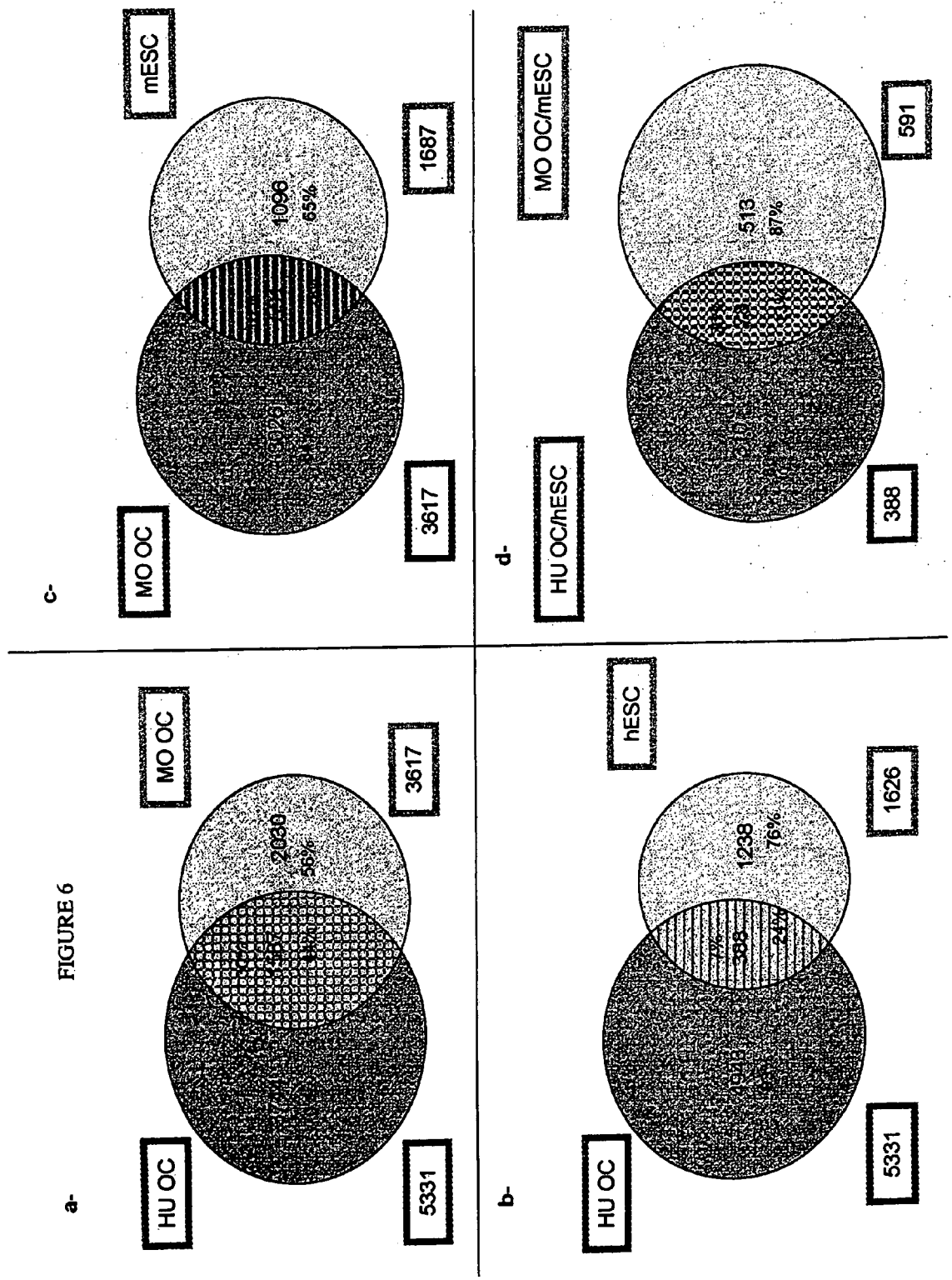
FIG. 6 contains Venn diagrams depicting intersection of differentially expressed genes in human and mouse oocytes and ESCs.
Figure 10:
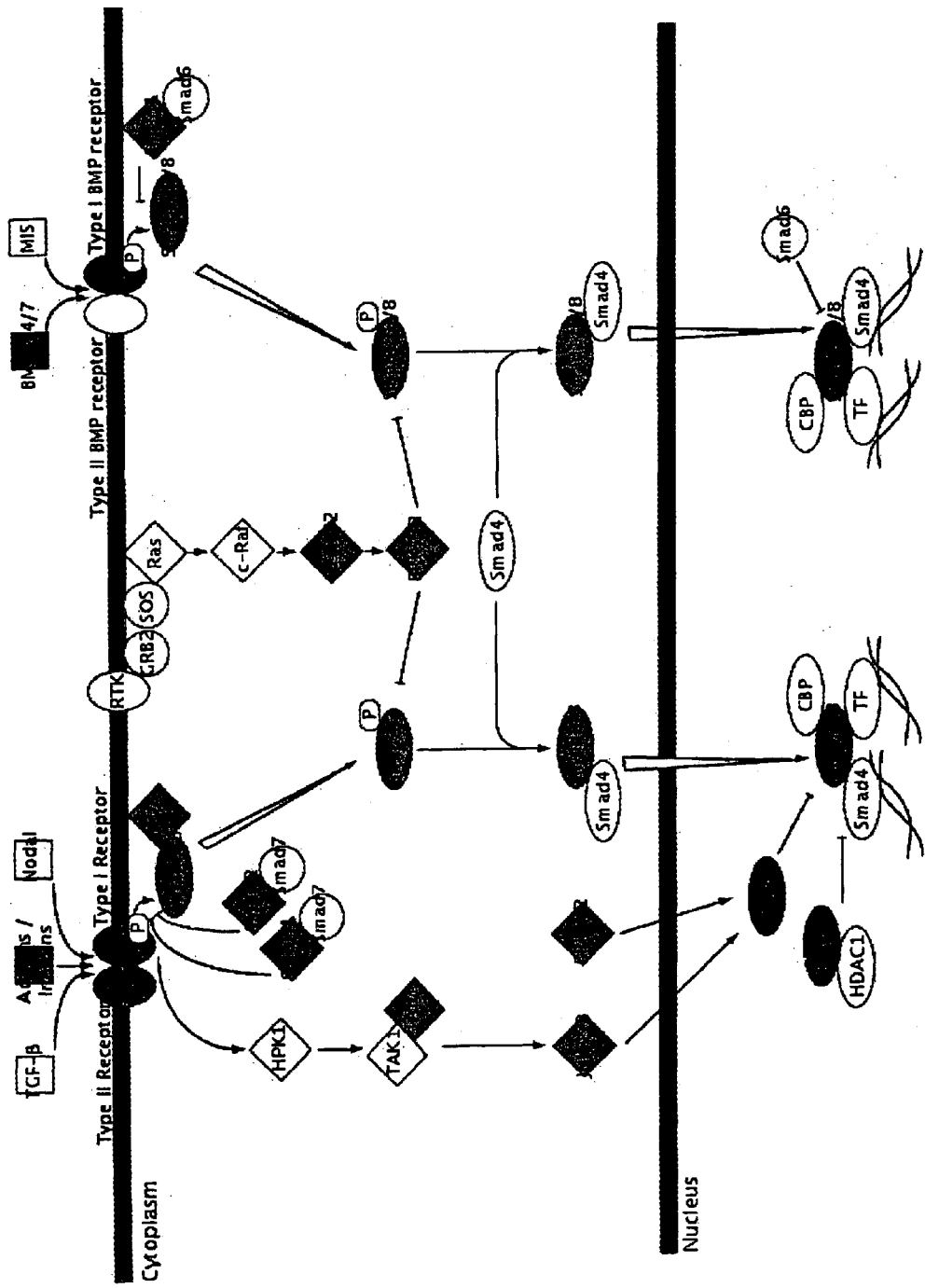
FIG. 10 contains genes differentially expressed in human oocytes corresponding to TGF-beta signaling pathway.
Figure 11:
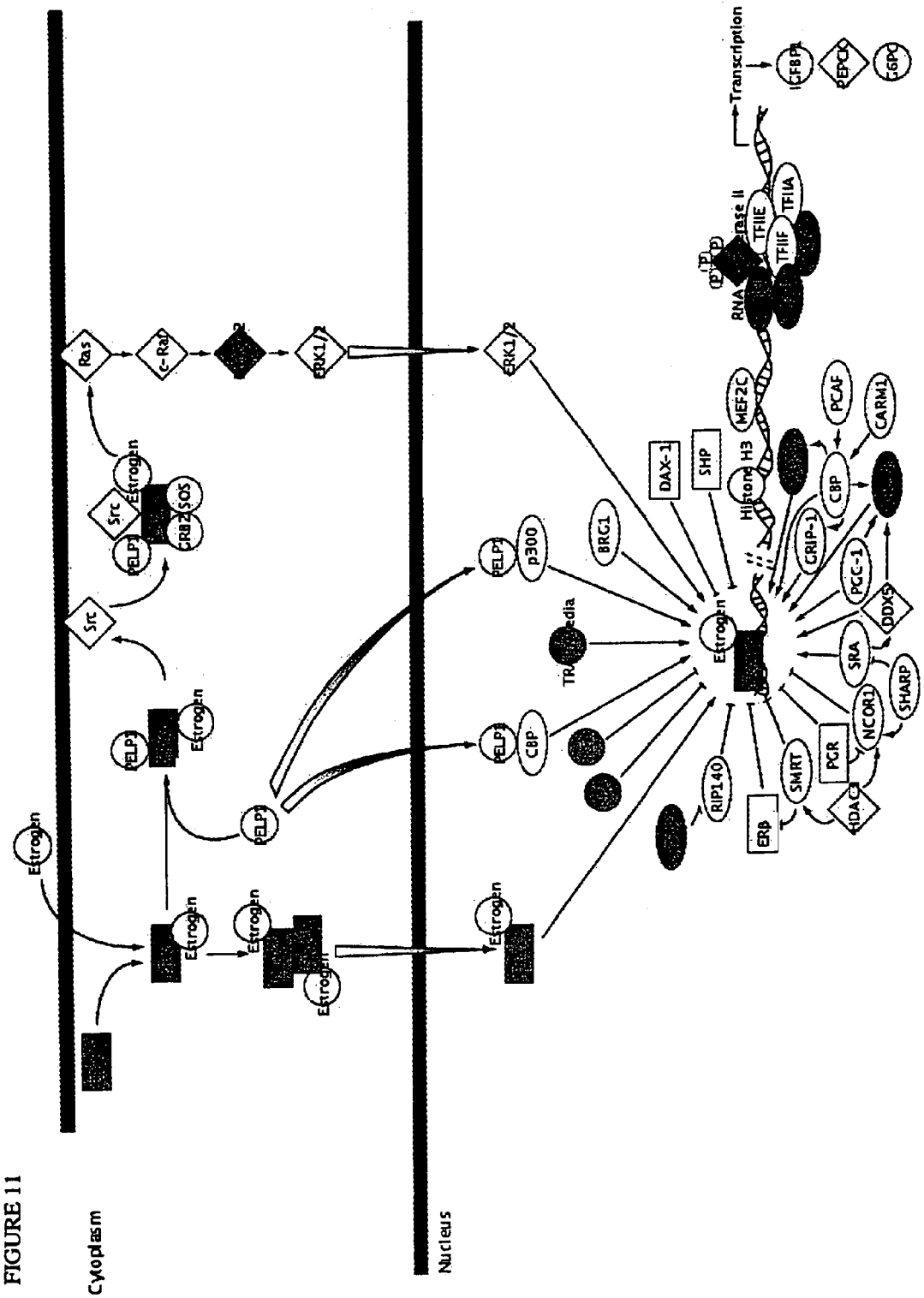
FIG. 11 contains gene that are differentially expressed in human and mouse oocytes that are in the estrogen receptor signaling pathway.

Mouse has been the best model for genetic studies and several groups have already reported the transcriptome analysed of mouse oocytes. (39) In an effort to find differences and similarities between the human and mouse oocyte, we compared our human oocyte transcriptome results with that of mouse oocyte transcriptome derived from data of Su et al. (35) The intersection of the two transcriptomes yielded a set of 1587 genes to be common in both mouse and human oocytes, indicating genes of conserved function in mammalian oocytes (FIG. 6a, Supplementary dataset 5). Table S2 shows the functional characterization of 16 of the top 100 intersected genes which have functions described in mouse oocytes. Many of these genes relate to oocyte maturation, from the first meiotic division to MII arrest, encompassing various controls of cell cycle checkpoints and cellular machinery for DNA segregation and cell division. Using the Ingenuity software to analyze the intersection of these two datasets we found that the estrogen receptor (ER) signaling pathway is represented in human and mouse oocytes (FIG. 6) Genes significantly upregulated in this pathway were CTBP2, ESR1, GTFH1, GTF2H2, MAP2K1, NCOA1, NCOA3, PCQAP, PHB2, POLR2C, POLR2J, RBM9, TAF3, TAF4, TAF4B, TAF5, TAF6, TAF12, and TBP. Recent studies in knockout models for aromatase have shown that estrogen is not required for the generation of preimplantation embryos. (40) However, our study suggests that in the oocyte some genes associated with the ER pathways are transcribed, perhaps in response to hormonal stimulation during folliculogenesis and oocyte maturation. Like with the EGF pathway, it remains to be determined whether the ER pathway has a role during preimplantation development in human embryos.

Considering thr High Degree of Similarity

EXAMPLE 2

Description

Phase I: At the clinic, embryologists will remove the cumulus cells of two eggs and fertilize them. Embryos will be transferred to the uterus of a woman and cumulus cells sent to the laboratory for analysis. Once the cells arrive to the laboratory, RNA will be isolated and microarray analysis performed using Affymetrix platform. Pregnancy tests will be done by ultrasound on day 30 and embryonic sacs counted. There will be three kinds of outcomes: 1) 0 sacs; 2) 1 sac and 3) 2 sacs. A minimum of 30 volunteer women will participate during this phase. Ten with no sacs, ten with one sac and ten with 2 sacs. Pregnancy data will be correlated with gene expression obtained from the cumulus cells isolated from those same eggs. One hundred genes that directly correlate with pregnancy —either by upregulation or downregulation—will be further analyzed using real time RT-PCR. The best 20 genes that correlate with pregnancy (positively or negatively) will be called "pregnancy signature" and used for later testing at the clinic.

Phase II: Blind validation of genes in the pregnancy signature. At the clinic, the embryologist will isolate RNA from cumulus cells from each oocyte that will be later fertilized. Half of the RNA will be sent to our laboratory and the rest will be used for real time RT-PCR analysis to be performed on site. Gene expression of the "pregnancy signature" will be measured. Embryologists will transfer embryos without knowing the outcome of gene expression analysis. One hundred women will be asked to participate as volunteers in this part of the study. At the time pregnancy results are obtained, the study will be unmasked and results from each individual will be correlated with gene expression analysis. We anticipate that the "pregnancy signature" put forward in phase 1 will be validated during this phase.

Alternative Strategy: In the event of an unexpected outcome i.e., the pregnancy signature is not validated; microarray analysis will be run once more using the RNA provided by the clinic in phase 2. It is anticipated that having 100 more samples will result in the identification of a clear pattern of gene expression in cumulus cells from eggs capable (or non-capable) of generating a healthy pregnancy/baby.

Using microarray analysis as described above, the genes identified infra were found to be differentially expressed by cumulus cells obtained from eggs of women donors. The expression of those particular genes which correlate to pregnancy (positive or negative) will establish a "pregnancy signature", i.e., genes the expression or absence of expression of which correlates to a positive pregnancy outcome and "infertility signature", i.e., specific genes the expression or absence of expression correlate to fertility problems or abnormalities.

This is effected preferably by microarray analysis. For example, comparison of expression between two samples on filter arrays may be performed by comparing nucleic acids obtained from normal oocyte cells to those obtained from a donor suspected of having ovarian dysfunction that renders oocytes pregnancy incompetent on two duplicate filters or alternatively a single filter may be used that is stripped and hybridized sequentially.

Direct comparison of gene expression in two samples can be achieved on glass arrays by labeling the two samples with different fluorophores. This technique allows the evolution of repression of gene expression as well as induction of expression. The two fluorescently-labeled cDNAs are then mixed and hybridized on a single glass or filter array. Glass arrays have the advantage of allowing the simultaneous analysis of two samples on the same array under the same hybridization conditions.

Gene arrays containing sequences of genes implicated in pregnancy ("pregnancy signature") will allow high-throughput screening of individuals for diagnostic purposes or tailor-made treatments.

Arrays of polynucleotides, the expression of which corresponds to, or are complementary to the sequences of genes identified by the method of the invention therefore provide a further aspect of the invention. Such an array will include at least two nucleic acid sequences, preferably at least 10, and more preferably at least 20, e.g., 50 genes or more that correspond to the sequence of, or are complementary to genes, the expression of which (positive or negative) the positive pregnancy outcome in cells obtained from oocyte donors, e.g., women suspected to have ovarian dysfunction as a result of disease, age, and the like. Protein arrays form a further aspect of the invention and will contain polypeptides encoded by such pregnancy signature genes or antibodies which bind thereto.

Recent developments in the field of protein and antibody arrays allow the simultaneous detection of a large number of proteins.

EXAMPLE 3

Figure 12:
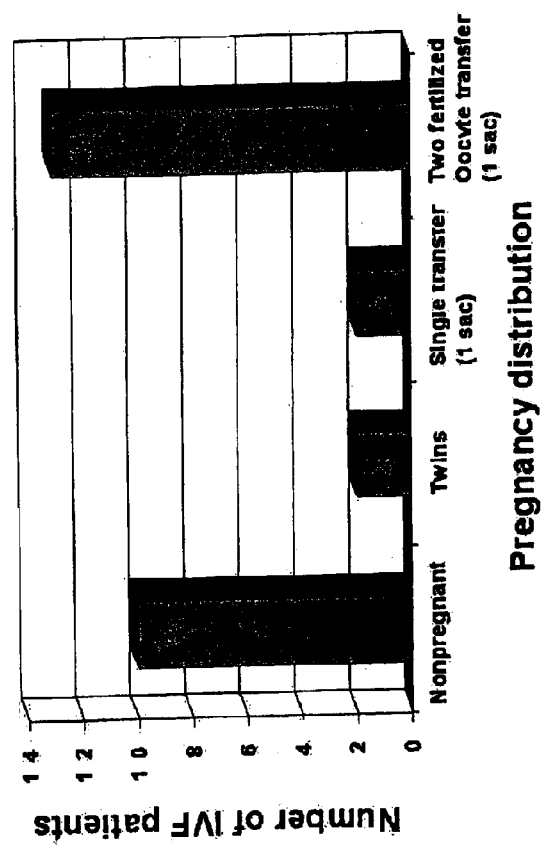
FIG. 12 contains progeny distribution of 27 analyzed in vitro fertilization (IVF) patients.

Identification of 3 Pregnancy Signature Genes which are Differentially Expressed by Cumulus Cells and wherein the Expression Levels of which Correlate to Pregnancy Outcome of Associated Human Oocytes There are no prior reports describing correlations between overall gene expression in cumulus cells and pregnancy establishment of human embryos. A study essentially as described in Example 2 was conducted to identify differentially expressed genes between cumulus cells surrounding competent and noncompetent oocytes using Affymetrix GeneChip technology. To achieve this goal cumulus cells were classified according to pregnancy outcome of their matching oocytes following in vitro fertilization (IVF) treatments. The cumulus cells from 2 oocytes per patient undergoing IVF treatment were lysed and the oocytes were fertilized and transferred to the recipient women, 2 embryos per recipient with the exception of 2 that received a single embryo. Total RNA isolated from the cumulus cell lysates was amplified by the novel amplification protocol described supra that combined template-switching PCR and T7-based amplification methods. A total of 52 cumulus cell samples were analyzed from 27 donors (FIG. 12). A gene-by-gene mixture model analysis was used to compare microarray measurements of gene expression on cumulus cells between pregnant and non-pregnant patients. 2,604 differential expressed genes were considered as potential discriminant candidates of competent and noncompetent oocytes.

Figure 13:
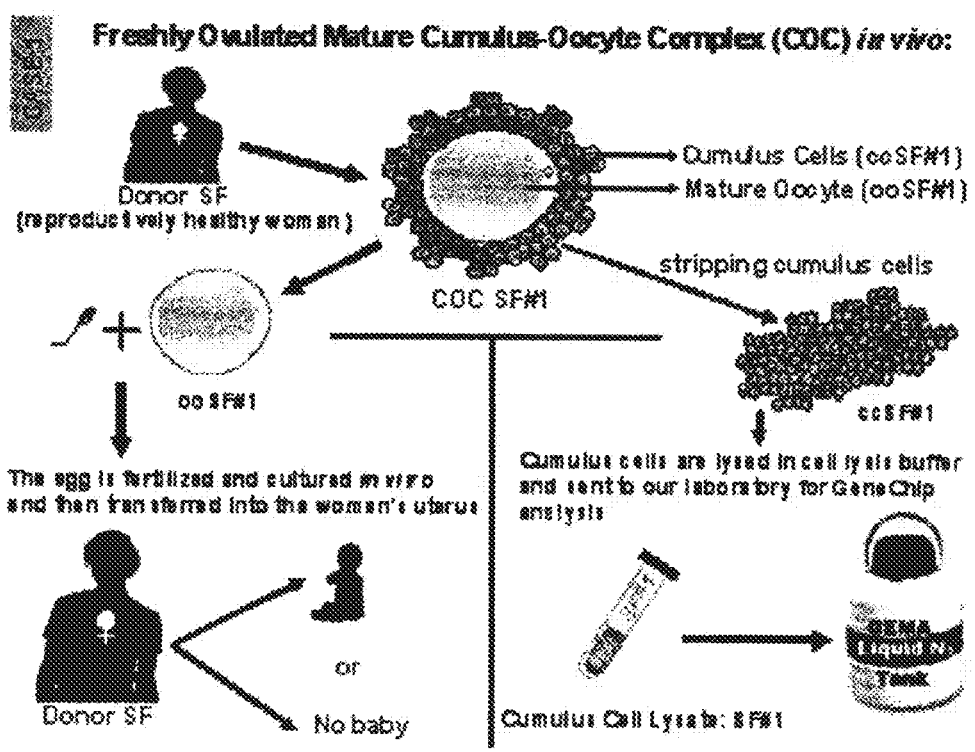
FIG. 13 contains a detailed flow chart describing the steps of the invention starting from the IVF clinic to the gene expression results. Panel A illustrates a sample collection from freshly ovulated mature cumulus-oocyte complex in vivo. Panel B shows quality and quantity checking of total RNA from 4 different cumulus cell lysates.
Figure 13:
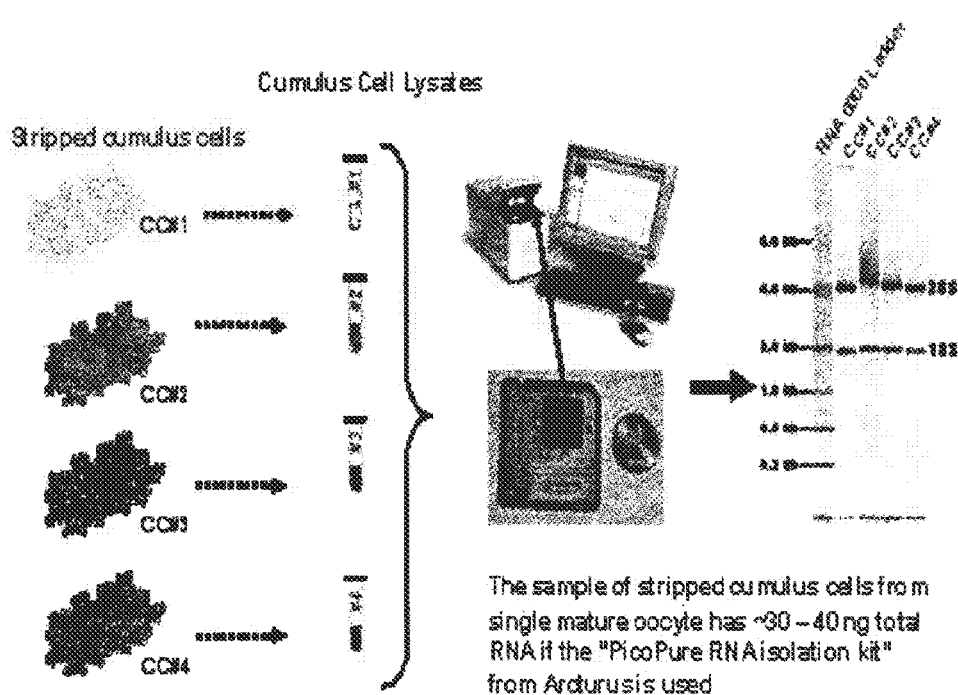
Figure 14:
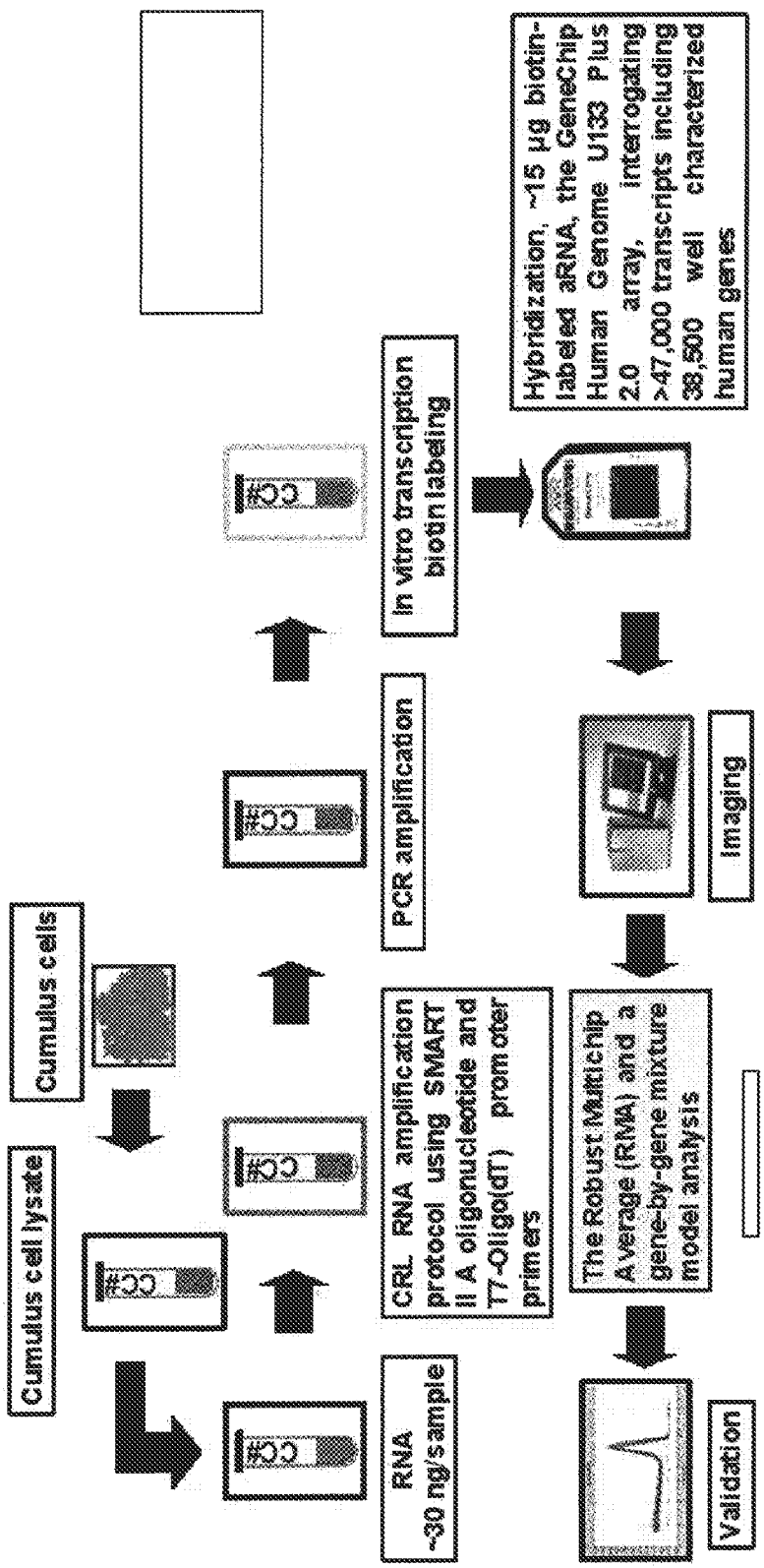
FIG. 14 depicts schematically the experimental design of the protocol in more detail than FIG. 1.
Figure 15:
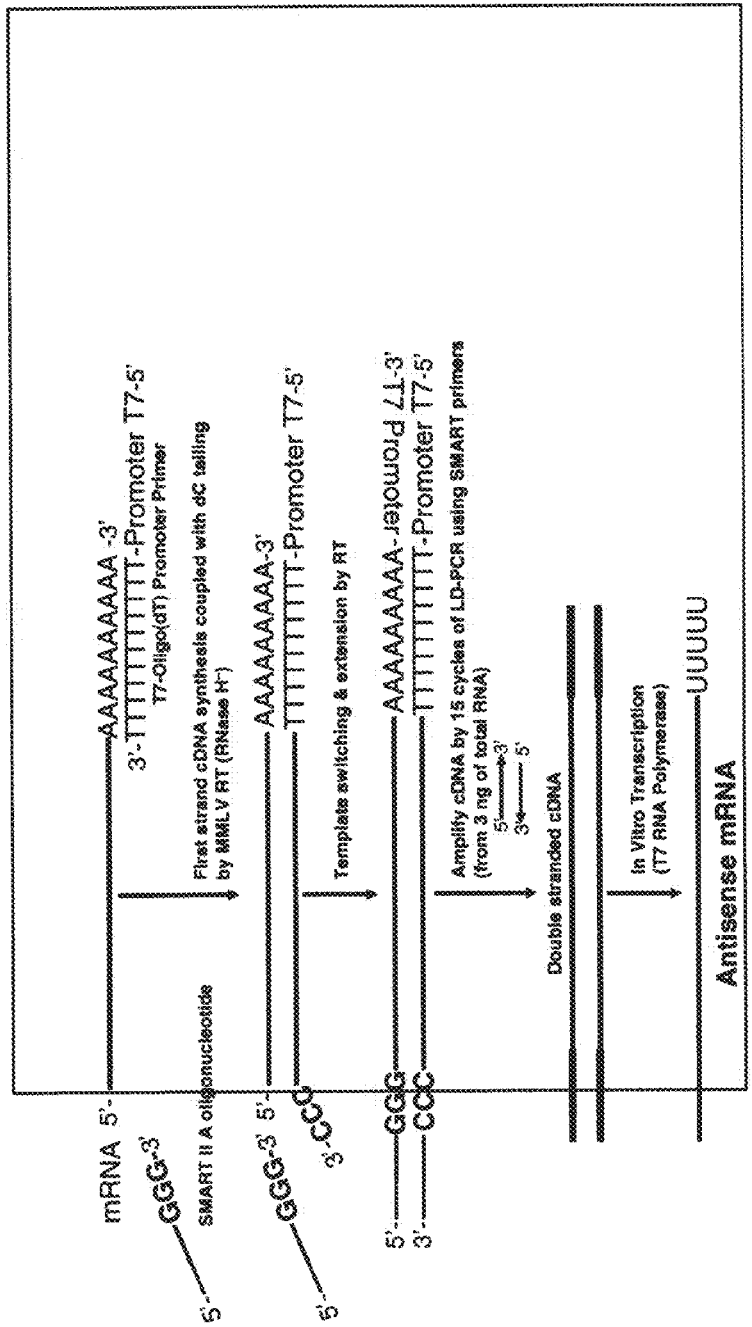
FIG. 15 contains a summary of CRL RNA amplification protocol described herein. Panel B shows the means of validating amplication fidelity. Figure discloses SEQ ID NO: 517.
Figure 15:
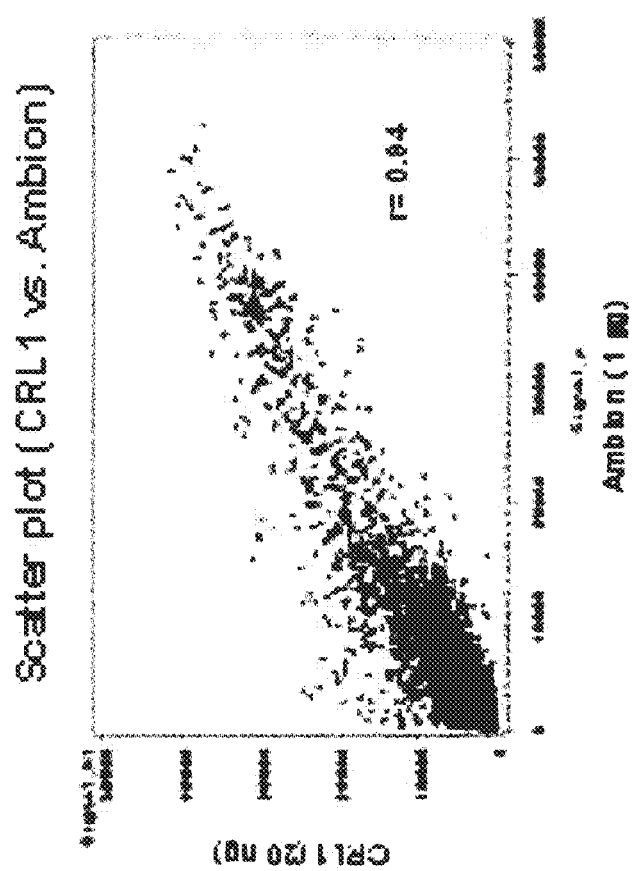

A flow chart of the specific procedures used is contained in FIG. 13 which shows how the quality and quantity of total RNA from different cumulus cell lysates is verified. The Experimental Design is also depicted schematically in FIG. 14 and the CRL amplification protocol and a scatter plot of the obtained results by the CRL amplification versus another method (Ambion) is contained in FIG. 15.

Figure 16:
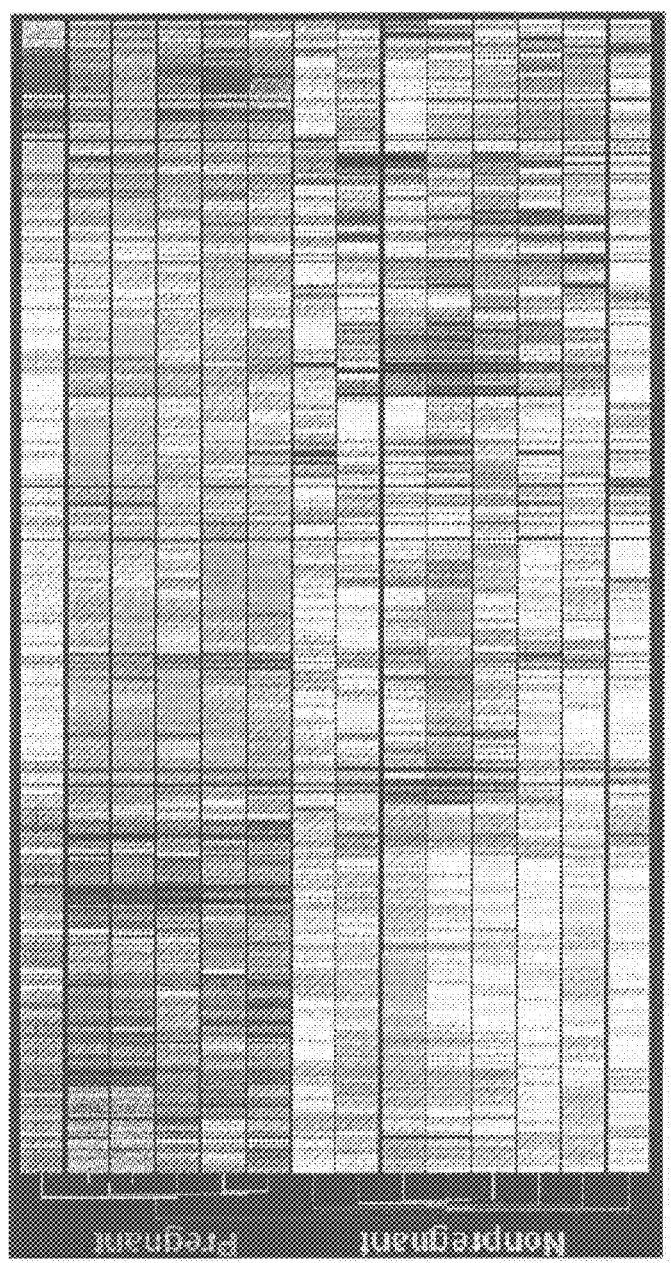
FIG. 16 shows clustering of samples using genes that are called present on 4 pregnant and 4 non-pregnant donor samples (442 probe sets).

As shown in FIG. 16 a comparison of the differential expression profiles of genes by cumulus cells of oocytes that give rise to pregnancies from 4 pregnant donor samples versus 4 donor samples that did not give rise to pregnancy reveals a clustering of samples using genes that are called present on the 4 pregnancy donor samples and 4 non-pregnant donor samples (442 probe sets).

Figure 17:
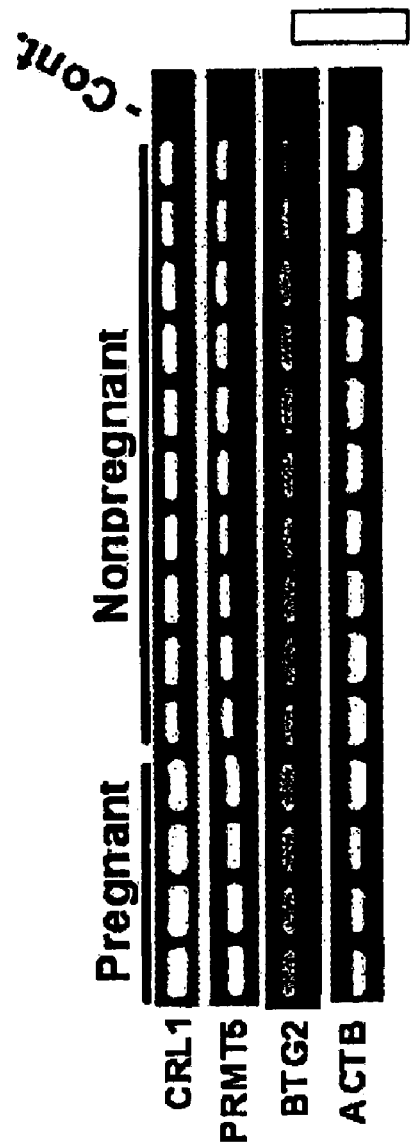
FIG. 17 contains experimental patterns of 3 candidate pregnancy markers in cumulus cells that resulted in pregnancy versus no pregnancy.

FIG. 17 contains the expression patterns of 3 candidate pregnancy marker genes in cumulus cells that produced pregnancy versus non-pregnancy. Additionally, FIG. 18 contains a Table containing the top 10 functional gene categories over-represented in differentially expressed genes between cumulus cells emanating from oocytes that produce pregnancies versus those that failed to produce pregnancies. Gene ontology and biological process and molecular function as detected by EASE when oocyte expressed genes were compared to the genes represented in the GeneChip array.

These results provide the first known comprehensive expression baseline (transcriptome) for the genes which are expressed in the human cumulus cells that surround a pregnancy-competent oocyte. As discussed, these genes may serve as markers for the quality and pregnancy outcome of the oocyte and can be used to monitor and optimize the factors that are related to developmental competence, such as patient specific medical treatments and medical conditions, hormone treatments, and embryo culture conditions. In addition, the effective development of pregnancy markers such as the genes which are contained in FIG. 19 can increase the probability of a healthy pregnancy and viable birth; reduce the chances of multiple births, physical and emotional burden, and the costs in treatments and hospital stays. Additionally, identifying these genes may facilitate an understanding of the underlying biology and help explain how the levels of expression of these genes may impact or cause female infertility.

TABLE-US-00001 LENGTHY TABLE REFERENCED HERE US20070238111A1-20071011-T00001 Please refer to the end of the specification for access instructions.

TABLE-US-00002 LENGTHY TABLE The patent application contains a lengthy table section. A copy of the table is available in electronic form from the USPTO web site. An electronic copy of the table will also be available from the USPTO upon request and payment of the fee set forth in 37 CFR 1.19(b)(3).

Sequence CWU 0 SQTB SEQUENCE LISTING The patent application contains a lengthy "Sequence Listing" section. A copy of the "Sequence Listing" is available in electronic form from the USPTO web site. An electronic copy of the "Sequence Listing" will also be available from the USPTO upon request and payment of the fee set forth in 37 CFR 1.19(b)(3).

Lengthy table referenced here

US07858308-20101228-T00001

Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US07858308B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07858308B2). An electronic copy of the "Sequence Listing" will also be available from the USPTO upon request and payment of the fee set forth in 37 CFR 1.19(b)(3).

The invention claimed is:

1. A method of identifying human oocytes that are capable of giving rise to a viable pregnancy when fertilized comprising the following steps: (i) obtaining at least one cumulus cell associated with an oocyte; (ii) assaying the expression of at least one gene by said at least one cumulus cell, the expression of which correlates to the capability of an oocyte associated with said cumulus cell to yield a viable pregnancy upon fertilization and transferal into a suitable uterine environment; and (iii) identifying, based on the level of expression of said at least one gene by said cumulus cell, whether said oocyte is potentially capable of yielding a viable pregnancy upon fertilization and transferal into a suitable uterine environment and wherein said at least one gene identified includes a gene selected from the group consisting of arginine methyl transferase (PRMT5), B-cell translocation gene 2 (BTG2), and beta actin gene (ACTB), that is expressed on average at elevated amounts in cumulus cells derived from oocytes that give rise to viable progeny versus those which do not and determining based on the level of expression of said at least one gene whether to use said oocyte in an in vitro fertilization (IVF) procedure.

2. The method of claim 1 wherein the expression of at least 10 genes, the expression of which correlates to the capability of an oocyte to potentially yield a viable pregnancy are measured.

3. The method of claim 2, wherein the expression of at least 15 genes, the expression of which correlates to the capability of an oocyte to potentially yield a viable pregnancy are identified.

4. The method of claim 3, wherein the expression of at least 20 genes, the expression of which correlates to the capability of an oocyte to potentially yield a viable pregnancy are identified.

5. The method of claim 4, wherein the expression of at least 20 to 50 genes, the expression of which correlates to the capability of an oocyte to potentially yield a viable pregnancy are identified.

6. The method of claim 5, wherein the expression of at least 50 to 100 genes, the expression of which correlates to the capability of an oocyte to potentially yield a viable pregnancy are identified.

7. The method of claim 1 wherein the method of assaying gene expression uses a method that monitors differential gene expression.

8. The method of claim 7 wherein said method comprises indexing differential display reverse transcriptase polymerase chain reaction (DDRT-PCR).

9. The method of claim 1, wherein the oocyte is obtained from a woman who is at least 25 years old.

10. The method of claim 1, wherein the oocyte is obtained from a woman who is at least 30 years old.

11. The method of claim 1, wherein the oocyte is obtained from a woman who is at no more than 35 years old.

12. The method of claim 1, wherein the oocyte is obtained from a woman who is at least 40 years old.

13. The method of claim 1, wherein an aberrant expression of said at least one gene is correlated to a condition selected from menopause, cancer, ovarian dysfunction, ovarian cyst, autoimmune disorder and hormonal dysfunction.

14. The method of claim 1, wherein gene expression is detected by real-time polymerase chain reaction (RT-PCR).

* * * * *